United States Patent
Tobler et al.

(10) Patent No.: US 7,781,615 B2
(45) Date of Patent: Aug. 24, 2010

(54) PROCESS FOR THE PREPARATION OF AMINES

(75) Inventors: Hans Tobler, Basel (CH); Harald Walter, Basel (CH); Camilla Corsi, Basel (CH); Josef Ehrenfreund, Basel (CH); Fanny Giordano, Muenchwilen (CH); Martin Zeller, Muenchwilen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 12/096,796

(22) PCT Filed: Dec. 11, 2006

(86) PCT No.: PCT/EP2006/011885
§ 371 (c)(1),
(2), (4) Date: Sep. 23, 2008

(87) PCT Pub. No.: WO2007/068417
PCT Pub. Date: Jun. 21, 2007

(65) Prior Publication Data
US 2009/0221856 A1 Sep. 3, 2009

(30) Foreign Application Priority Data
Dec. 12, 2005 (EP) ................... 05027072
Apr. 21, 2006 (EP) ................... 06008248

(51) Int. Cl.
*C07C 211/45* (2006.01)
*C07C 211/48* (2006.01)
*C07C 209/10* (2006.01)
*C07C 209/68* (2006.01)
*C07C 17/266* (2006.01)
*C07C 25/22* (2006.01)

(52) U.S. Cl. .................. 564/308; 564/405; 564/407; 564/415; 570/183; 570/190; 570/204

(58) Field of Classification Search ............ None
See application file for complete search history.

(56) References Cited

FOREIGN PATENT DOCUMENTS

WO 2004018438 3/2004
WO 2004035589 4/2004

OTHER PUBLICATIONS

Tanida et al: "Relative Reactivities of some Benzocyclenes in Aromatic Nitration and Electrophilic Side-Chain Reaction," Journal of the American Chemical Society, vol. 87, No. 21, 1965, XP009075487, p. 4803, right hand column, line 1; figures Chart II.
Robert A. Snow et al: "Analysis of bridging regioselectivity operative in photorearrangement of ortho-substituted benzonorbornadienes," Journal of the American Chemical Society, American Chemical Society, Washington, DC, US, vol. 99, No. 11, May 25, 1977, pp. 3734-3744, XP002271785, ISSN: 0002-7863, p. 3734-p. 3737.
Hartwig, et al., III.3.2 Palladium-Catalyzed Amination of Aryl Halides and Related Actions; Handbook of Organopalladium Chemistry for Organic Synthesis, vol. 1, pp. 1051-1096, (2002).
Yang, Bryant et al., Palladium-catalyzed amination of aryl halides and sulfonates; Journal of Organometallic Chemistry; 576, pp. 125-146 (1999).

Hillier, Anna C., et al., Catalytic cross-coupling reactions medicated by palladium/nucleophilic carbene systems; Journal of Organometallic Chemistry; 653, pp. 69-82 (2002).
Coe, Jotham, et al., Fomration of 3-Halobenzyne: Solvent Effects and Cycloaddition Adducts; Organic Letters, vol. 6, No. 10, p. 1589-1592 (2004).
Sapountzis, Ioannis, et al., Angew. Chemistry, 116, 4464-446 (2004).

*Primary Examiner*—Brian J Davis
(74) *Attorney, Agent, or Firm*—William Mulholland

(57) ABSTRACT

The present invention relates to a novel a process for the preparation of the compound of the general formula (I), wherein $R^1$ and $R^2$ are independently H or $C_{1-6}$ alkyl, which comprises treating with a reducing agent either a compound of the general formula (II), wherein $R^1$ and $R^2$ have the meanings given for the compound of the formula (I), $R^3$ is H or $C_{1-4}$alkyl and Ph is phenyl, or a compound of the general formula (III), wherein $R^1$, $R^2$, $R^3$ and Ph have the meanings given for the compound of the formula (II), the reducing agent being effective to cleave the benzyl moiety Ph-CH($R^3$)— from the benzylamino moiety PhCH($R^3$)NH— in the compound of the formula (II) or in the compound of the formula (III) to leave an amino group and, in addition, in the case of the compound of the formula (III), to reduce both the 2,3-double bond and the double bond joining the $R^1R^2C$— moiety to the 9-position of the benzonorbornene ring to single bonds. It also relates to processes for the preparation of the compounds (II) and (III) and their precursors and to the compounds (II) and (III) themselves and certain of their precursors, which are novel compounds. The compounds (I) are useful for the preparation of various fungicidal heterocyclylcarboxylic acid benzonorbornen-5-yl-amides.

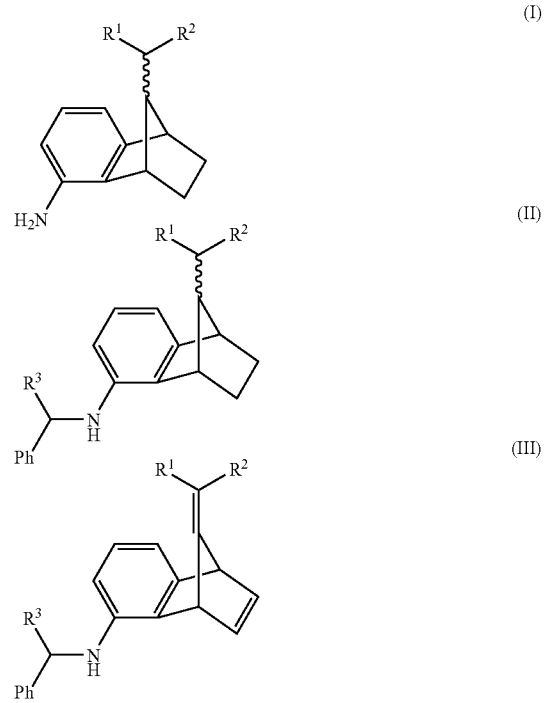

27 Claims, No Drawings

PROCESS FOR THE PREPARATION OF AMINES

This application is a 371 of International Application No. PCT/EP2006/011885 filed Dec. 11, 2006, which claims priority to EP 05027072.7 filed Dec. 12, 2005, and EP 06008248.4 filed Apr. 21, 2006, the contents of which are incorporated herein by reference.

The present invention relates to a novel process for preparing certain 5-amino-benzonorbornenes and their use for preparing carboxylic acid benzonorbornenyl-amides, which are useful as microbiocides and especially as fungicides.

Various heterocyclyl-carboxylic acid benzonorbornen-5-yl-amides, methods for their preparation and their use as microbiocides are described in WO 04/035589. According to 04/035589, these amides may be prepared as outlined in Scheme 1 below.

Scheme 1

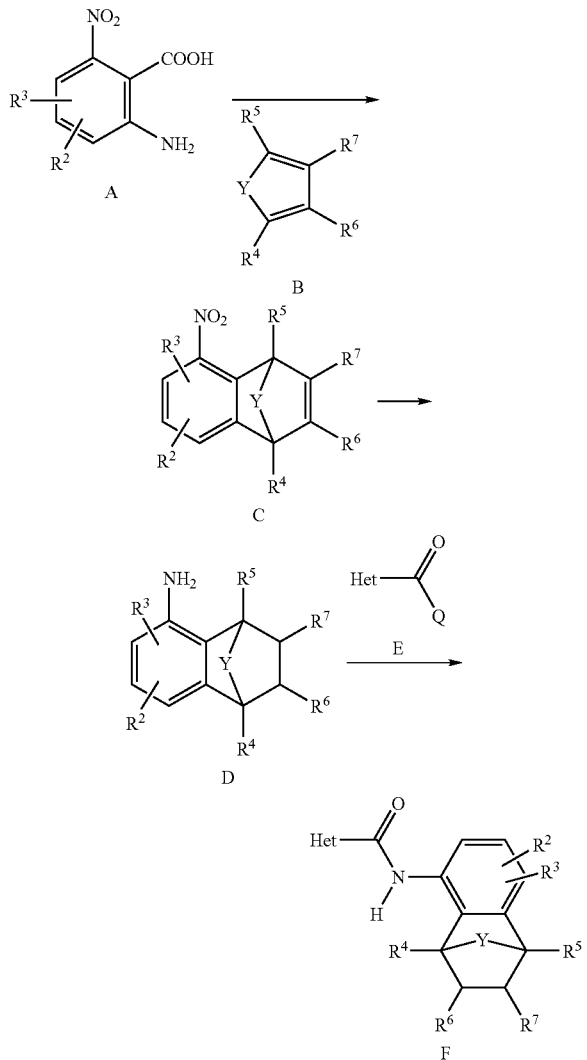

In the synthesis shown in Scheme 1, a 3-nitrobenzene, generated from a 6-nitro-anthranilic acid (A), is reacted with a cyclic 1,4-diene (B), such as 5-isopropyl-cyclopentadiene, to form a 5-nitro-benzonorbornadiene (C) in a Diels-Alder reaction. Under standard catalytic reduction conditions (for example, using Raney nickel or palladium on carbon in a solvent such as methanol), both the 5-nitro group and the 2,3-double bond of the 5-nitro-benzonorbornadiene (C) are reduced to form the 5-amino-benzonorbornene (D). Reaction of the 5-amino-benzonorbornene (D) with a heterocyclyl-carboxylic acid or heterocyclyl-carboxylic acid derivative (E), where Q may be hydroxyl, fluoro, chloro or bromo, in a solvent such as dichloromethane gives a fungicidal heterocyclyl-carboxylic acid benzonorbornen-5-yl-amide (F). An example of (D) is 5-amino-9-isopropyl-benzonorbornene, which is a precursor of an amide of, for example, 3-difluoromethyl-1-methyl-1H-pyrazole-4-carboxylic acid.

The problem with the synthesis outlined in Scheme 1 is that a number of unwanted isomeric impurities are formed. For example, in the preparation of the 5-nitro-benzonorbornadiene (C), where $R^4$, $R^5$, $R^6$ and $R^7$ are all H and Y is CH-isopropyl, by the Diels-Alder reaction, the following regio-isomers are formed:

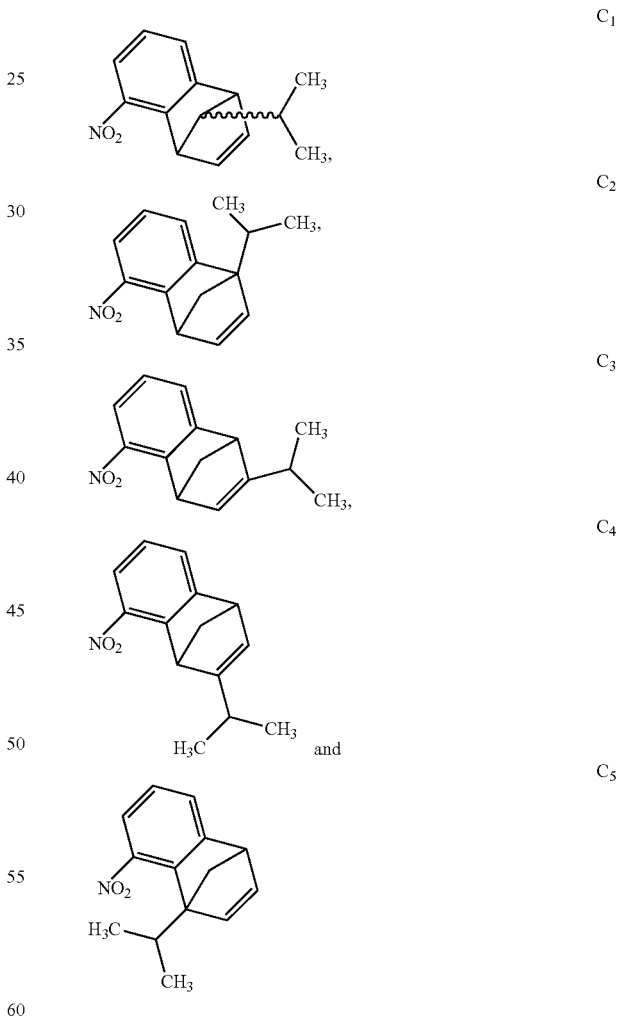

Unfortunately, the desired isomer $C_1$ is formed in relatively low yield. While the unwanted isomers may be removed, either at the end of the Diels-Alder reaction or at a later stage, by conventional techniques such as fractional crystallisation or fractional distillation or by chromatographic methods, this synthetic route is not well suited to large scale production.

A solution to this problem is provided by the present process which enables the 5-amino-benzonorbornene (D) to be prepared in an economically favourable manner in good yield and quality.

Thus, according to the present invention, there is provided a process for the preparation of the compound of the general formula (I):

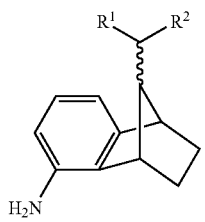

(I)

wherein $R^1$ and $R^2$ are independently H or $C_{1-6}$ alkyl, which comprises treating with a reducing agent either a compound of the general formula (II):

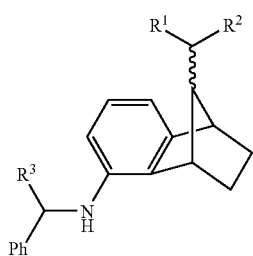

(II)

wherein $R^1$ and $R^2$ have the meanings given for the compound of the formula (I), $R^3$ is H or $C_{1-4}$ alkyl and Ph is phenyl, or a compound of the general formula (III):

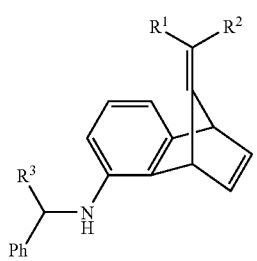

(III)

wherein $R^1$, $R^2$, $R^3$ and Ph have the meanings given for the compound of the formula (II), the reducing agent being effective to cleave the benzyl moiety Ph-CH($R^3$)— from the benzylamino moiety PhCH($R^3$)NH— in the compound of the formula (II) or in the compound of the formula (III) to leave an amino group and, in addition, in the case of the compound of the formula (III), to reduce both the 2,3-double bond and the double bond joining the $R^1R^2C$— moiety to the 9-position of the benzonorbornene ring to single bonds.

Each alkyl moiety is a straight or branched chain and, depending on whether it contains 1 to 4 or 1 to 6 carbon atoms, is, for example, methyl, ethyl, n-propyl, n-butyl, n-pentyl, n-hexyl, iso-propyl, sec-butyl, iso-butyl, tert-butyl, neo-pentyl, n-hexyl or 1,3-dimethylbutyl.

$R^1$ and $R^2$ are independently H or $C_{1-6}$ alkyl. They may both be H or one may be H and the other a $C_{1-6}$ alkyl group or they may both be the same or different alkyl groups. Of particular interest are compounds where $R^1$ and $R^2$ are selected from H, methyl and ethyl, and especially those compounds where both $R^1$ and $R^2$ are methyl.

$R^3$ is H or $C_{1-4}$ alkyl. Most conveniently, it is H.

The compound of the general formula (II) may be in either of the two stereo-isomeric forms (IIa) or (IIb) or mixtures of both in any proportions, (IIa) being the syn epimer and (IIb) the anti epimer:

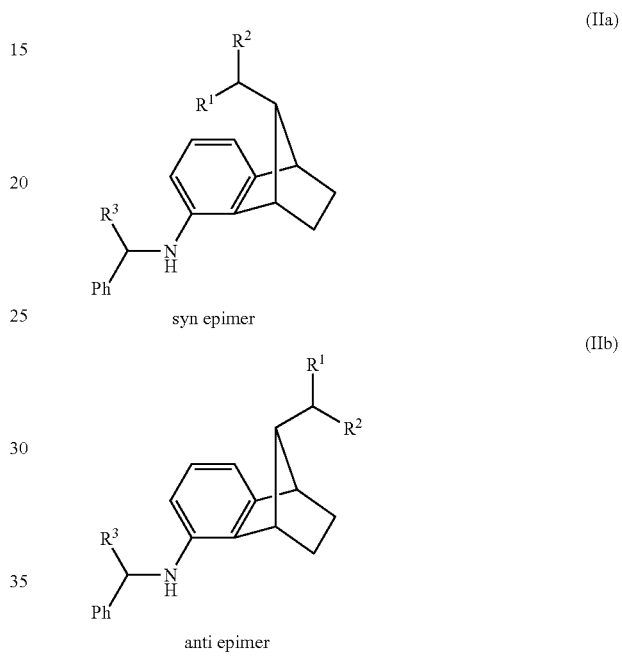

The syn epimer (IIa) can exist in two stereoisomeric forms: the syn (+) form and the syn (−) form. The invention covers the use of both forms and mixtures of both in any proportions. The anti epimer (IIb) can exist in two stereoisomeric forms: the anti (+) form and the anti (−) form. The invention covers the use of both forms and mixtures of both in any proportions.

The compound of the general formula (III) can exist in two stereoisomeric forms: the (+) form and the (−) form. The invention-covers the use of both forms and mixtures of both in any proportions.

The compound of the general formula (I) may be in either of the two stereo-isomeric forms (Ia) or (Ib) or mixtures of both in any proportions, (Ia) being the syn epimer and (Ib) the anti epimer:

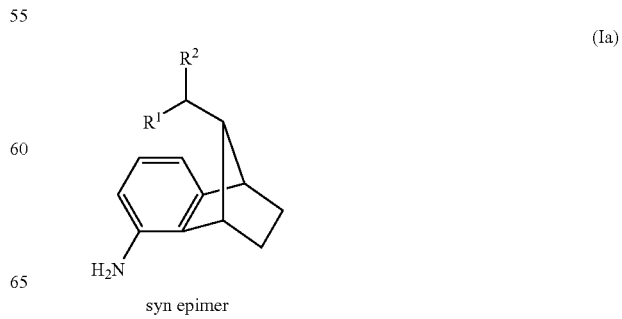

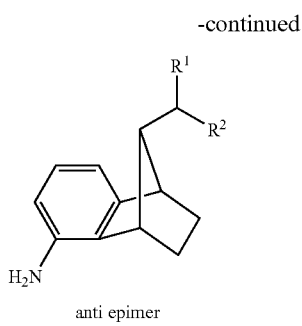

anti epimer (Ib)

The syn epimer (Ia) can exist in two stereoisomeric forms: the syn (+) form and the syn (−) form. The invention covers the preparation of both forms and mixtures of both in any proportions. The anti epimer (Ib) can exist in two stereoisomeric forms: the anti (+) form and the anti (−) form. The invention covers the preparation of both forms and mixtures of both in any proportions.

Reductive cleavage of the benzyl moiety of the compound of the formula (II) may be carried out using any effective reducing agent. Particularly effective is hydrogen in the presence of a metal hydrogenation catalyst, for example a rhodium catalyst or preferably a palladium catalyst such as palladium on carbon.

The amount of reducing agent used will normally be from 1 to 5, typically from 1 to 1.3 mole equivalents of compound (II). Where the reducing agent is hydrogen, the amount of catalyst used will normally be from 0.001 to 0.5, typically from 0.01 to 0.1 mole equivalents of compound (II). A metal catalysed hydrogenation will normally yield a mixture of the syn and anti epimers (IIa) and (IIb).

The reduction is conveniently carried out in an inert solvent, for example, an alcohol such as methanol, ethanol, n-propanol or 2-propanol or a protic solvent such as tetrahydrofuran, tert-butyl methyl ether, dioxane, ethyl acetate or dimethoxyethane or a mixture of such solvents. Typically the solvent is tetrahydrofuran or methanol.

The temperature at which the reduction is carried out is not critical. Suitably it is carried out at from 0° C. to 80° C., typically from 0° C. to 25° C., and conveniently at ambient temperature. Similarly the pressure is not critical and the reduction may be performed at elevated or reduced pressure, but is conveniently performed at ambient pressure.

The time taken to complete the reduction will depend, inter alia, on the reaction conditions and scale, but will normally take from between 1 to 48 hours and typically from 1 to 6 hours.

Reductive cleavage of the benzyl moiety of the compound of the formula (III) may also be carried out using any effective reducing agent. The type of reducing agent, catalyst, solvent and reaction conditions described above in respect of the reduction of the compound of the formula (II) are equally effective for the reduction of the compound of the formula (III) except that the amount of reducing agent used will normally be from 3 to 6, typically from 3 to 3.3 mole equivalents of compound (III), because of the additional reduction of the two double bonds as well as the cleavage of the benzyl moiety. The amount of catalyst used, the temperature and pressure of reaction and the time the reaction takes will be much the same as for the reduction of the compound of the formula (II).

The compound of the general formula (II) may be prepared by a process that forms another aspect of the present invention. This process comprises reacting a compound of the general formula (IV):

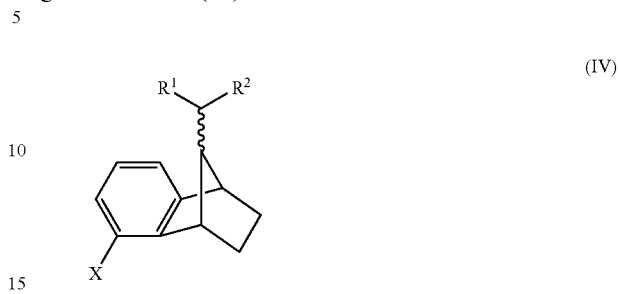

(IV)

wherein $R^1$ and $R^2$ have the meanings given above and X is chloro or bromo, with a benzylamine of the general formula (V):

(V)

wherein $R^3$ and Ph have the meanings given above, in the presence of a base and a catalytic amount of at least one palladium complex.

Suitable bases for carrying out the above process include alkoxides such as sodium and potassium tert-butoxides and sodium methoxide and ethoxide, and inorganic bases such as carbonates, for example potassium, sodium and caesium carbonates, hydroxides, for example sodium and potassium hydroxides, and phosphates, for example potassium phosphate. Particularly useful are alkoxides, especially sodium tert-butoxide.

When using sodium or potassium hydroxide as the base, a phase transfer catalyst such as cetyltrimethylammonium bromide may be added.

The amount of base used is typically from 1 to 3 mole equivalents of the compound (IV), for example 1 to 2 mole equivalents.

The palladium complex used in the process will generally be formed from a palladium precursor and at least one suitable ligand. Where the process is carried out in a solvent, the complex will normally be soluble in the solvent. In the context of this process palladium complexes expressly include those consisting of cyclic organic palladium compounds ("palladacycles") and secondary phosphine ligands.

The palladium complex may be used as a robust, pre-formed species or may be formed in situ. Typically it is made by reacting a palladium precursor with at least one suitable ligand. In the case of incomplete transformations, residual amounts of the palladium precursor or ligand may be present undissolved in the reaction mixture.

Useful palladium precursors may be chosen from palladium acetate, palladium chloride, palladium chloride solution, palladium$_2$-(dibenzylidene acetone)$_3$ or palladium-(dibenzylidene acetone)$_2$, palladium-tetrakis(triphenylphosphine), palladium/carbon, palladium dichlorobis(benzonitrile), palladium-(tris-tert-butylphosphine)$_2$ or a mixture of palladium$_2$-(dibenzylidene acetone)$_3$ and palladium-(tris-t-butylphosphine)$_2$.

Useful ligands are, for example, tertiary phosphine ligands, N-heterocyclic carbene ligands and phosphinic acid ligands. Tertiary phosphine ligands are generally of two types: monodentate and bidentate ligands. A monodentate ligand may occupy one palladium coordination site while a bidentate ligand occupies two coordination sites and hence is able to chelate the palladium species.

The following are examples of tertiary phosphine, N-heterocyclic carbene and phosphinic acid ligands and a palladacycle with a secondary phosphine ligand.

(A) Monodentate Phosphine Ligands:

Tri-tert-butylphosphine, tri-tert-butylphosphonium tetrafluoroborate ("P(tBu)$_3$HBF$_4$"), tris-ortho-tolylphosphine ("P(oTol)$_3$"), tris-cyclohexylphosphine ("P(Cy)$_3$"), 2-di-tert-butyl-phosphino-1,1'-bisphenyl ("P(tBu)$_2$BiPh"), 2-di-cyclohexyl-phosphino-1,1'-bisphenyl ("P(Cy)$_2$BiPh"), 2-dicyclohexylphosphino-2',4',6'-tri-isopropyl-1,1'-bisphenyl ("x-Phos"), and tert-butyl-di-1-adamantyl-phosphine ("P(tBu)(Adam)$_2$").

More information about monodentate phosphine ligands can be found in US-2004-0171833.

(B) Bidentate Tertiary Phosphine Ligands:

(B1) Biphosphine Ligands:

(B1.1) Ferrocenyl-Biphosphine Ligands ("Josiphos" Ligands):

1,1'-bis(diphenylphosphino)ferrocene (dppf), 1,1'-bis(di-tert-butylphosphino)-ferrocene, (R)-(−)-1-[(S)-2-(bis(4-trifluoromethylphenyl)phosphino)ferrocenyl]ethyl-di-tert-butyl-phosphine, (R)-(−)-1-[(S)-2-(di(3,5-bis-trifluoromethylphenyl)phosphino)ferrocenyl]ethyl-dicyclohexylphosphine, (R)-(−)-1-[(S)-2-(di(3,5-bis-trifluoromethylphenyl)phosphino)-ferrocenyl]ethyldi(3,5-dimethylphenyl)phosphine, (R)-(−)-1-[(S)-2-(dicyclohexylphosphino)-ferrocenyl]ethyldi-tert-butylphosphine, (R)-(−)-1-[(S)-2-(dicyclohexylphosphino)ferrocenyl]-ethyldicyclohexylphosphine, (S)-(+)-1-[(R)-2-(dicyclohexylphosphino)ferrocenyl]ethyl-dicyclohexylphosphine, (S)-(+)-1-[(R)-2-(dicyclohexylphosphino)ferrocenyl]ethyldiphenyl-phosphine, (R)-(−)-1-[(S)-2-(bis(3,5-dimethyl-4-methoxyphenyl)phosphino)ferrocenyl]-ethyldicyclohexylphosphine, (S)-(+)-1-[(R)-2-(difurylphosphino)ferrocenyl]ethyldi-3,5-xylylphosphine, (R)-(−)-1-[(S)-2-(diphenylphosphino)ferrocenyl]ethyldi-tert-butylphosphine, (S)-(+)-1-[(R)-2-(diphenylphosphino)ferrocenyl]ethyldi-tert-butylphosphine, (R)-(−)-1-[(S)-2-(diphenylphosphino)ferrocenyl]ethyldicyclohexylphosphine, (R)-(+)-1-[(R)-2-(diphenylphosphino)ferrocenyl]ethyldicyclohexylphosphine, (S)-(+)-1-[(R)-2-(diphenylphosphino)-ferrocenyl]ethyldicyclohexylphosphine, (R)-(−)-1-[(S)-2-(dicyclohexylphosphino)ferrocenyl]-ethyldiphenylphosphine, (R)-(−)-1-[(S)-2-(diphenyl)phosphino)ferrocenyl]ethyldi(3,5-dimethylphenyl)phosphine, (R)-(−)-1-[(S)-2-(di-tert-butyl-phosphino)ferrocenyl]ethyl-di-o-tolylphosphine

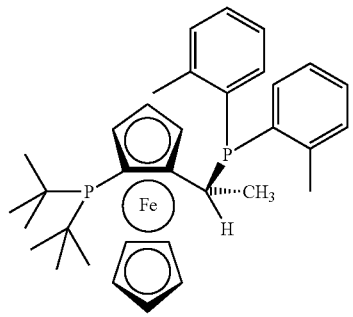

(R)-(−)-1-[(S)-2-(bis(3,5-dimethyl-4-methoxyphenyl)phosphino)ferrocenyl]-ethyl-di-tert-butylphosphine

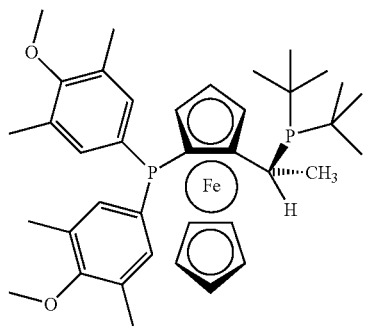

(R)-(−)-1-[(S)-2-(diethylphosphino)ferrocenyl]-ethyl-di-tert-butylphosphine

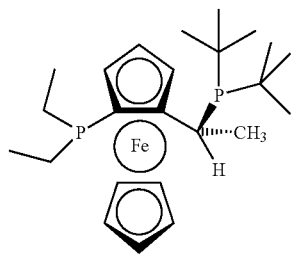

(R)-(−)-1-[(S)-2-(P-methyl-P-isopropyl-phosphino)ferrocenyl]ethyldicyclohexylphosphine

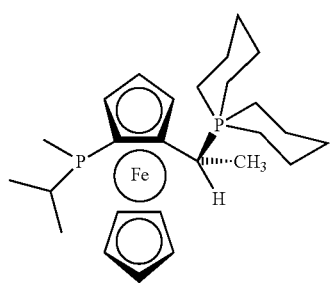

(R)-(-)-1-[(S)-2-(P-methyl-P-phenyl-phosphino)ferrocenyl]ethyl-di-tert-butylphosphine

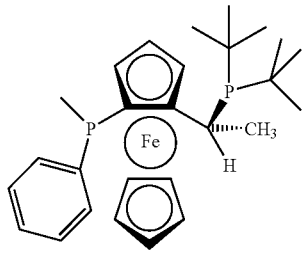

and racemic mixtures thereof, especially racemic mixtures of 1-[2-(di-tert-butylphosphino)-ferrocenyl]ethyl-di-o-tolylphosphine, 1-[2-(dicyclohexylphosphino)ferrocenyl]ethyldi-tert-butylphosphine and 1-[2-(diphenylphosphino)ferrocenyl]ethyldicyclohexylphosphine.

(B1.2) Binaphthyl-Bisphosphine Ligands:

2,2'bis(diphenylphosphino)-1,1'-binaphthyl ("BINAP"), R-(+)-2,2'-bis(di-p-tolylphosphino)-1,1'-binaphthyl ("Tol-BINAP"), racemic 2,2'-bis(di-p-tolylphosphino)-1,1'-binaphthyl ("racemic Tol-BINAP").

(B1.3) 9,9-Dimethyl-4,5-bis(diphenyl-phosphino)-xanthene ("Xantphos").

(B2) Aminophosphine2 Ligands:

(B2.1) Biphenyl Ligands:

2-dicyclohexylphosphino-(N,N-dimethylamino)-1,1'-biphenyl ("PCy$_2$NMe$_2$BiPh")

2-di-tert-butylphosphino-(N,N-dimethylamino)-1,1'-biphenyl ("P(tBu)$_2$NMe$_2$BiPh").

(C) N-Heterocyclic Carbene Ligands:

1,3-bis-(2,6-diisopropylphenyl)-imidazolium chloride ("I—Pr"), 1,2-bis(1-adamantyl)-imidazolium chloride ("I-Ad") and 1,3-bis-(2,6-methylphenyl)-imidazolium chloride ("I-Me").

(D) Phosphinic Acid Ligands:

di-tert-butyl-phosphinoxide.

(E) Palladacycles Containing a Secondary Phosphine Ligand:

the complex of the formula (A-1)

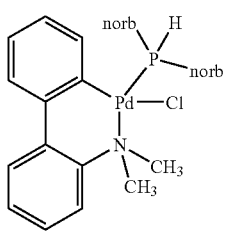

(A-1)

where "norb" is norbornyl, and the complex of the formula (A-2)

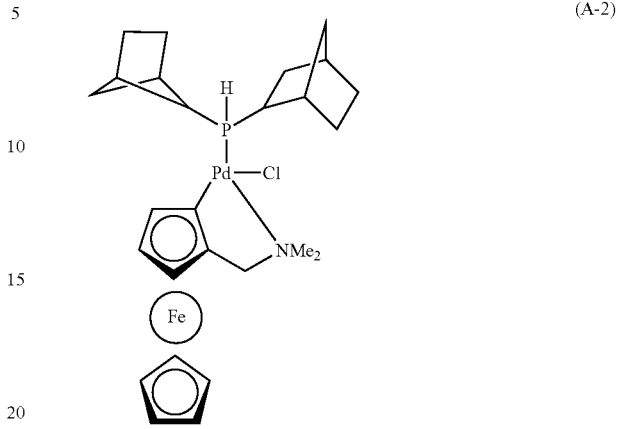

(A-2)

The palladium complex (A-1) is described in Synlett., 2549-2552 (2004) under the code name "SK-CC01-A". The complex (A-2) is described in Synlett. (ibid) under the code name "SK-CC02-A".

Further examples of palladium complexes containing phosphinic acid ligands are described in J. Org. Chem. 66, 8677-8681 under the code names "POPd", "POPd2" and "POPD1". Further examples of palladium complexes containing N-heterocyclic carbene ligands are naphthoquinone-1,3-bis(2,6-diisopropylphenyl)imidazole-2-ylidene-palladium (["Pd—NQ-IPr]$_2$"), divinyl-tetramethylsiloxane-1,3-bis(2,6-diisopropylphenyl)imidazole-2-ylidene-palladium ("Pd—VTS-IPr"), 1,3-bis(2,6-diisopropylphenyl)imidazole-2-ylidene-palladium dichloride ("Pd—Cl—IPr"), 1,3-bis(2,6-diisopropylphenyl)imidazole-2-ylidene-palladium diacetate ("Pd—OAc—IPr"), allyl-1,3-bis(2,6-diisopropylphenyl)imidazole-2-ylidene-palladium chloride ("Pd—Al—Cl—IPr") and a compound of the formula (A-3):

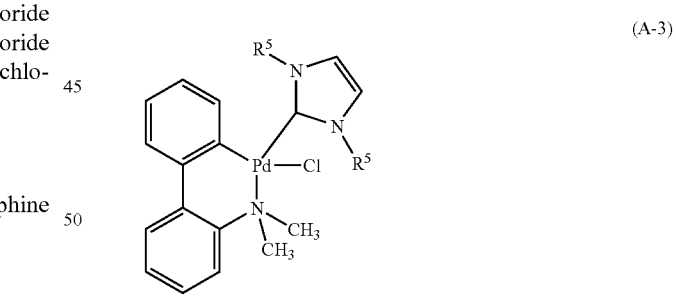

(A-3)

where R$^5$ is 2,6-diisopropylphenyl or 2,4,6-trimethylphenyl. More information about [Pd—NQ-IPr]$_2$, Pd—VTS-IPr, Pd—Cl—IPr, Pd—OAc—IPr and Pd—Al—Cl—IPr can be found in Organic Letters, 4, 2229-2231 (2002) and Synlett., 275-278, (2005) More information about the compound of formula (A-3) can be found in Organic Letters, 5, 1479-1482 (2003).

A single palladium complex or a mixture of different palladium complexes may be used in the process for preparing the compound of the general formula (II).

Palladium precursors that are particularly useful for the formation of the palladium complexes are those selected from palladium acetate, palladium$_2$-(dibenzylidene acetone)$_3$, palladium-(dibenzylidene acetone)$_2$, palladium chloride solution or a mixture of palladium$_2$-(dibenzylidene acetone)$_3$ and palladium-(tris-tert.-butylphosphine)$_2$. Palladium acetate is especially useful, as is palladium chloride.

At least one ligand is used for the formation of the palladium complex. Normally the palladium complex will have at least one ligand chosen from a monodentate tertiary phosphine ligand, a bidentate tertiary phosphine ligand and a N-heterocyclic carbene ligand, and typically at least one ligand chosen from a ferrocenyl-biphosphine ligand, a binaphthyl-bisphosphine ligand and an aminophosphine ligand.

Particularly suitable are palladium complexes that contain at least one ligand selected from tri-tert-butylphosphine, P(tBu)$_3$HBF$_4$, P(oTol)$_3$, P(Cy)$_3$, P(tBu)$_2$BiPh, P(Cy)$_2$BiPh, x-Phos, P(tBu)(Adam)$_2$, (R)-(−)-1-[(S)-2-(dicyclohexylphosphino)ferrocenyl]ethyldi-tert-butyl-phosphine, racemic 1-[2-(dicyclohexylphosphino)ferrocenyl]ethyldi-tert-butylphosphine, (R)-(−)-1-[(S)-2-(di-tert-butyl-phosphino)ferrocenyl]ethyldi-o-tolylphosphine, racemic 1-[2-(di-tert-butyl-phosphino)ferrocenyl]ethyldi-o-tolylphosphine, dppf, 1,1'-bis(di-tert-butyl-phosphino)-ferrocene, (R)-(−)-1-[(S)-2-(diphenylphosphino)ferrocenyl]ethyldicyclohexyl-phosphine, racemic 1-[2-(diphenylphosphino)ferrocenyl]ethyldicyclohexylphosphine, (R)-(−)-1-[(S)-2-(diphenylphosphino)ferrocenyl]ethyldi-tert-butylphosphine, BINAP, Tol-BINAP, racemic Tol-BINAP, Xantphos, PCy$_2$NMe$_2$BiPh, P(tBu)$_2$NMe$_2$BiPh, I—Pr, I-Ad and I-Me, and a palladium complex of formula (A-3), where R$^5$ is 2,6-diisopropylphenyl or 2,4,6-trimethyl-phenyl.

Preferred are palladium complexes with at least one ligand selected from tri-tert-butylphosphine, P(tBu)$_3$HBF$_4$, P(tBu)$_2$BiPh, P(Cy)$_2$BiPh, x-Phos, (R)-(−)-1-[(S)-2-(dicyclohexylphosphino)ferrocenyl]ethyldi-tert-butylphosphine, racemic 1-[2-(dicyclohexylphosphino)ferrocenyl]ethyldi-tert-butylphosphine, (R)-(−)-1-[(S)-2-(di-tert-butyl-phosphino)ferrocenyl]ethyldi-o-tolylphosphine, racemic 1-[2-(di-tert-butyl-phosphino)ferrocenyl]ethyldi-o-tolylphosphine, dppf, PCy$_2$NMe$_2$BiPh and I—Pr.

Of especial interest are palladium complexes that contain at least one ligand selected from the following groups:

(i) tri-tert-butylphosphine, P(tBu)$_3$HBF$_4$, P(tBu)$_2$BiPh, P(Cy)$_2$BiPh, x-Phos, PCy$_2$NMe$_2$BiPh and I—Pr;

(ii) tri-tert-butylphosphine, P(tBu)$_3$HBF$_4$, PCy$_2$NMe$_2$BiPh and I—Pr;

(iii) tri-tert-butylphosphine and P(tBu)$_3$HBF$_4$; and (iv) (R)-(−)-1-[(S)-2-(dicyclohexylphosphino)ferrocenyl]ethyldi-tert-butylphosphine and racemic 1-[2-(dicyclohexylphosphino)ferrocenyl]ethyldi-tert-butylphosphine.

Most preferred are palladium complexes that contain as a ligand PCy$_2$NMe$_2$BiPh, I—Pr, (R)-(−)-1-[(S)-2-(dicyclohexylphosphino)ferrocenyl]ethyldi-tert-butylphosphine or racemic 1-[2-(dicyclohexylphosphino)ferrocenyl]ethyldi-tert-butylphosphine.

A particularly preferred complex is one where the precursor is palladium chloride and the ligand is (R)-(−)-1-[(S)-2-(dicyclohexylphosphino)ferrocenyl]ethyldi-tert-butylphosphine.

The palladium complex is used in the preparation of the compound of formula (II) in a catalytic amount, normally in a molar ratio of from 1:10 to 1:10000 in respect to the compound of formula (IV), typically in a ratio of 1:100 to 1:1000, for example, 1:500 to 1:700 or about 1:600. The complex may be pre-formed or formed in situ by mixing together the precursor and ligand, which will generally be used in equimolar amounts, or thereabouts.

The compound of formula (V) used for reaction with the compound of the formula (IV) is conveniently benzylamine itself, where R$^3$ is H.

Conveniently, the compounds (IV) and (V) are employed in equimolar amounts or with an excess of the compound (V). For example, the amount of the compound of formula (V) used is suitably from 1 to 3 mole equivalents of the compound (IV), typically from 1 to 2 equivalents, for example, about 1.5 mole equivalents.

The preparation of the compound of the formula (II) is conveniently carried out in an inert organic solvent, which is preferably dry. Suitable solvents include 1,2-dimethoxyethane, di(ethylene glycol) dimethyl ether (diglyme), tert-butyl methyl ether, pentane, hexane, cyclohexane, tetrahydrofuran, dioxane, toluene or xylene, and mixtures thereof. Preferred solvents are diethyleneglycol dialkylethers having the general formula:

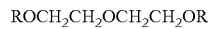

ROCH$_2$CH$_2$OCH$_2$CH$_2$OR wherein R is C$_{1-4}$ alkyl. Most convenient solvents are 1,2-dimethoxyethane or diglyme.

However, the process may be performed without a solvent. In this case the compound of formula (V) will normally be used in excess of the compound of formula (IV).

Whether or not a solvent is employed, the process may be performed at ambient or elevated temperatures, preferably in a range of from 50° C. to 200° C. and typically from 80° C. to 150° C. It may also be performed at ambient, elevated or reduced pressure, conveniently at ambient pressure.

The time the reaction takes will depend, inter alia, on the scale at which it is carried out, the reagents used and the reaction conditions. Normally, however, it will take from 1 to 48 hours, typically from 4 to 30 hours, for example, from 4 to 18 hours.

It may be beneficial to carry out the process in an inert gas atmosphere such as in an atmosphere of nitrogen or argon, most conveniently nitrogen.

Further information on the general conditions for carrying out the preparation the process for producing the compound of the formula (II) will be available to a skilled chemist in the literature relating to the preparation of anilines from halobenzenes by palladium-catalysed cross coupling reactions with alkyl amines. Review articles on such couplings have appeared in, for example, the *Handbook of Organopalladium Chemistry for Organic Synthesis*, Vol. 1, 1051-1096 (2002), the *Journal of Organometallic Chemistry*, 576, 125-146 (1999) and the *Journal of Organometallic Chemistry*, 653, 69-82 (2002).

The compound of the general formula (III) may be prepared by a process that forms yet another aspect of the present invention. This process comprises reacting a compound of the general formula (VI):

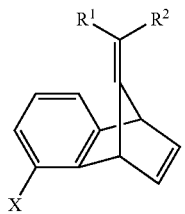
(VI)

wherein $R^1$ and $R^2$ have the meanings given above and X is chloro or bromo, with a benzylamine of the general formula (V):

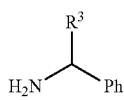
(V)

wherein $R^3$ and Ph have the meanings given above, in the presence of a base and a catalytic amount of at least one palladium complex.

The base, the palladium complex, the compound (V) and the process conditions are the same as described above for the process for preparing the compound (II) from the 5-chloro- or 5-bromo-benzobornene (IV). In this case, however, a particularly preferred palladium complex is one where the precursor is palladium chloride and the ligand is the carbene ligand I—Pr. Otherwise, all details described for the compound (II) process are equally applicable to the compound (III) process.

Where $R^1$ and $R^2$ are different, the compounds of the general formulae (III) and (IV) may exist as the E- or Z-isomers or as mixtures of both in any proportion.

As well as being useful for preparing the compound of the formula (I), the compound of the formula (III) may be used to prepare the compound of the formula (II).

Thus, in yet another aspect of the invention there is provided a process for the preparation of a compound of the general formula (II):

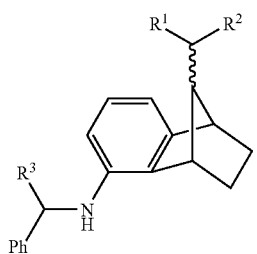
(II)

wherein $R^1$, $R^2$, $R^3$ and Ph have the meanings given above, which comprises treating a compound of the general formula (III):

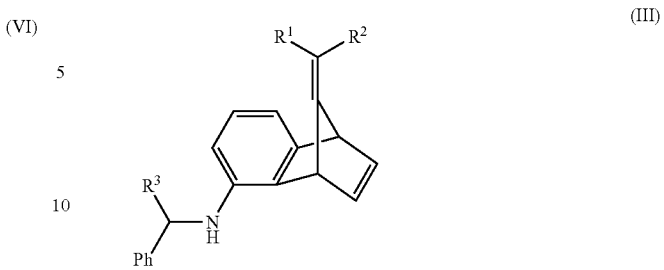
(III)

wherein $R^1$, $R^2$, $R^3$ and Ph have the meanings given above, with a reducing agent, the reducing agent being effective to reduce both the 2,3-double bond and the double bond joining the $R^1R^2C$— moiety to the 9-position of the benzonorbornene ring to single bond but to leave the $PhCH(R^3)NH$— moiety intact.

A suitable reducing agent for this process is hydrogen in the presence of a metal hydrogenation catalyst, such as a rhodium catalyst, for example, rhodium on carbon.

The amount of reducing agent used will normally be from 2 to 6 mole equivalents of the compound (I), typically from 2 to 2.3 mole equivalents.

The amount of catalyst used will normally be from 0.001 to 0.5 mole equivalents of the compound (III), typically from 0.01 to 0.1.

The reduction is conveniently carried out in an inert solvent, for example, an alcohol such as methanol, ethanol, n-propanol or 2-propanol or a protic solvent such as tetrahydrofuran, tert-butyl methyl ether, dioxane, ethyl acetate or dimethoxyethane or a mixture of such solvents. Typically the solvent is tetrahydrofuran or methanol.

The temperature at which the reduction is carried out is not critical. Suitably it is carried out at from 0° C. to 80° C., typically from 0° C. to 25° C., and conveniently at ambient temperature. Similarly the pressure is not critical and the reduction may be performed at elevated or reduced pressure, but is conveniently performed at ambient pressure to 4 bar pressure.

The time taken to complete the reduction will depend, inter alia, on the reaction conditions and scale, but will normally take from between 1 to 48 hours, typically from 1 to 6 hours.

The 5-chloro- or 5-bromo-benzonorbornene of the general formula (IV) may be prepared by a process which comprises treating a compound of the general formula (VI):

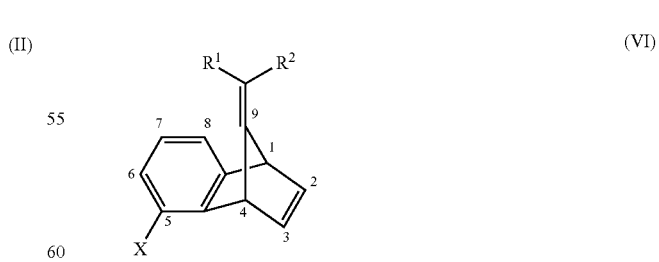
(VI)

wherein $R^1$ and $R^2$ have the meanings given above and X is chloro or bromo, with a reducing agent, the reducing agent being effective to reduce both the 2,3-double bond and the double bond joining the $R^1R^2C$— moiety to the 9-position of the benzonorbornene ring to single bonds.

A suitable reducing agent for this process is hydrogen in the presence of a metal hydrogenation catalyst, such as a Raney nickel, platinum on carbon, platinum(IV) oxide, palladium on carbon, rhodium on carbon, rhodium(III) oxide or a rhodium on alumina catalyst. Rhodium on carbon, palladium on carbon or platinum on carbon are ideal. In one embodiment of the invention, rhodium on carbon or palladium on carbon is used.

The amount of reducing agent used will normally be from 2 to 6 mole equivalents of the compound (VI), typically from 2 to 2.3 mole equivalents.

The amount of catalyst used will normally be from 0.01 to 50 mol % of the compound (VI), typically from 0.1 to 20 mol %.

The reduction is conveniently carried out in an inert solvent, for example, an alcohol such as methanol, ethanol, n-propanol or 2-propanol or a solvent such as tetrahydrofuran, ethyl acetate, toluene, tert-butyl methyl ether, dioxane, dimethoxyethane or dichloromethane or a mixture of such solvents. Typically the solvent is tetrahydrofuran, ethanol or methanol, preferably tetrahydrofuran or methanol.

The temperature at which the reduction is carried out is not critical. Suitably it is carried out at from 0° C. to 100° C., typically from 0° C. to 30° C., and conveniently at 20° C. to 25° C.

Similarly the pressure is not critical and the reduction may be performed at from 1 to 150 bar, normally at from 1 to 50 bar, typically from 1 to 25 bar, for example, from 1 to 10 bar.

The compound of the formula (IV) may be obtained as the syn or anti epimer or as a mixture of both. Normally it will be obtained as a mixture of the two epimers, their ratio depending, inter alia, on the particular hydrogenation catalyst chosen.

The 5-chloro- or 5-bromobenzobornadiene of the general formula (VI) may be prepared by a process which comprises reacting a halobenzyne of the formula (VII):

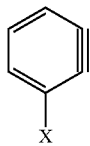
(VII)

wherein X is chloro or bromo, with a fulvene of the general formula (VIII):

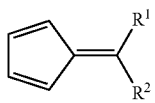
(VIII)

wherein $R^1$ and $R^2$ have the meanings given above, in an inert organic solvent.

Depending on how the halobenzyne (VII) is generated, the process is carried out in an organic solvent such as tetrahydrofuran, 1,4-dioxane, dimethoxyethane, diethyl ether, tert-butyl methyl ether, methyl-ethyl-ketone, ethyl acetate, methylacetate or an aromatic or aliphatic hydrocarbon, for example, toluene, xylene, benzene, hexane, pentane or a petroleum ether, and at a temperature of from −20° C. to +10° C., which may be elevated to ambient temperature or to a higher temperature to complete the reaction.

The 5-chloro- or 5-bromobenzonorbornadiene of the formula (VI) may be isolated by quenching the reaction mixture in an aqueous medium, for example, in saturated ammonium chloride solution, extracting the product in a solvent such as ethyl acetate, washing the solvent extract with, for example, brine and water, drying it and evaporating off the solvent to obtain the halobenzobornadiene (VI), which may be further purified by crystallisation from a solvent such as hexane.

The halobenzyne (VII) may be obtained by a process which comprises reacting a 1,2,3-trihalobenzene of the formula (IX) or (X):

(IX)

(X)

wherein X is chloro or bromo and Y is bromo or iodo, with an organometallic species such as a $C_{1-6}$ alkyl or phenyllithium or a $C_{1-6}$ alkyl- or phenylmagnesium halide in an inert atmosphere.

Preferably X is chloro.

The $C_{1-6}$ alkyl- or phenylmagnesium halide is preferably a chloride or bromide and more preferably iso-propylmagnesium chloride or bromide.

If a $C_{1-6}$ alkyl- or phenyllithium is used, the reaction is carried out in the presence of the fulvene (VIII) to give the 5-chloro- or 5-bromobenzobornadiene directly. In this case the reaction is carried out in a solvent such as toluene, benzene, hexane, pentane or petroleum ether at a temperature of −20° C. to 0° C., typically at −10° C. to 0° C. The reaction mixture may be allowed to warm to ambient temperature prior to isolation by quenching in an aqueous medium as described above.

If a $C_{1-6}$ alkyl- or phenylmagnesium halide is used, the 5-chloro- or 5-bromobenzobornadiene may be formed in a stepwise procedure, the halobenzyne (VII) being formed in a first step and the 5-chloro- or 5-bromobenzobornadiene being formed in a second step either by the subsequent addition of the fulvene (VIII) or by the subsequent addition to the fulvene (VIII). The first step reaction between the halobenzyne (IX) or (X) with the $C_{1-6}$ alkyl- or phenylmagnesium halide is carried out at a temperature of from −78° C. to 0° C., typically at −20° C. to −10° C. In the first case the subsequent fulvene addition at −20° C. to +10° C., typically at −10° C. to 0° C. The reaction is promoted by warming the mixture to ambient temperature or preferably to the reflux temperature of the solvent used. In the second case the subsequent addition to the fulvene is carried out at 20° C. to 100° C., typically at 70° C. to 95° C. The reaction is stirred an additional hour to complete the conversion.

Suitable solvents include tetrahydrofuran, 1,4-dioxane, dimethoxyethane, diethyl ether, tert-butyl methyl ether, hexane, petroleum ethers, pentane, benzene, toluene and xylene, preferably toluene, tetrahydrofuran or hexane. The 5-chloro- or 5-bromobenzobornadiene may then be isolated by quenching in an aqueous medium as described above.

The inert atmosphere in which the reaction is carried out is, for example, a nitrogen atmosphere.

Transformations of this type are described by J. Coe in *Organic Letters*, 6, 1589 (2004) or P. Knochel in *Angew. Chem.* 116, 4464 (2004).

1,2,3-trihalobenzenes of the formula (IX) or (X) are known and/or can be prepared by known methods. For example, 1-bromo-2,3-dichloro-benzenes may be prepared by the so-called Sandmeyer reaction from 2,3-dichloro-aniline. Such Sandmeyer reactions can be performed either by using an organic nitrite ester, such as tert-butyl nitrite or iso-pentyl nitrite, in an organic solvent, such as acetonitrile, in the presence of cupric bromide as brominating agent (as described in Journal of Organic Chemistry, 1977, 42, 2426-31) or by a two-step reaction involving diazotation in an acidic aqueous reaction media at temperatures of 0° C. to 15° C. using inorganic nitrite and then adding the reaction mixture to cuprous bromide solution (as described in Recueil des Travaux Chimiques des Pays-Bas et de la Belgique, 1932, 51, 98-113 and JP-6-2114-921).

6-Alkyl- or 6,6-dialkylfulvenes may be prepared as described by M. Neuenschwander et al, *Helv. Chim. Acta*, 54, 1037 (1971), *ibid* 48, 955 (1965), R. D. Little et al, *J. Org. Chem.* 49, 1849 (1984), I. Erden et al, *J. Org. Chem.* 60, 813 (1995) and S. Collins et al, *J. Org. Chem.* 55, 3395 (1990).

Fulvenes of the General Formula (VIII):

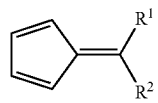

(VIII)

wherein $R^1$ and $R^2$ have the meanings given above, can be prepared by the reaction of cyclopenta-1,3-diene with a compound (VIIIa):

wherein $R^1$ and $R^2$ have the meanings given above, in the presence of a base. As a base pyrrolidine, morpholine or thiomorpholine is preferably used, more preferred is pyrrolidine. In such reactions 0.01 to 1 equivalents base can be used. Preferably 0.25 to 0.8 equivalents base are used.

Preparation of 6,6-dimethylfulvene 950 g (30 mol) methanol, 543 g (7.8 mol) acetone and 397 g (6 mol) cyclopentadiene are mixed and cooled to −5° C. 107 g (1.5 mol) pyrrolidine are carefully added. The reaction mixture is stirred for 2 hours at −5° C. The reaction is stopped by adding acetic acid and water. After phase separation, the organic phase is extracted with brine and the solvent is evaporated. 535 g of 6,6-dimethylfulvene are obtained (purity: 93%; yield: 78% of theory).

For convenience, the foregoing reactions are summarised in Scheme 2 below.

Scheme 2

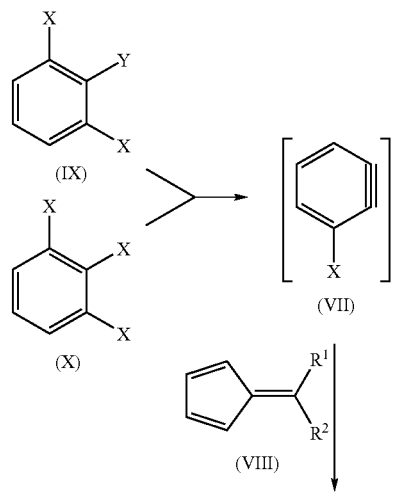

-continued

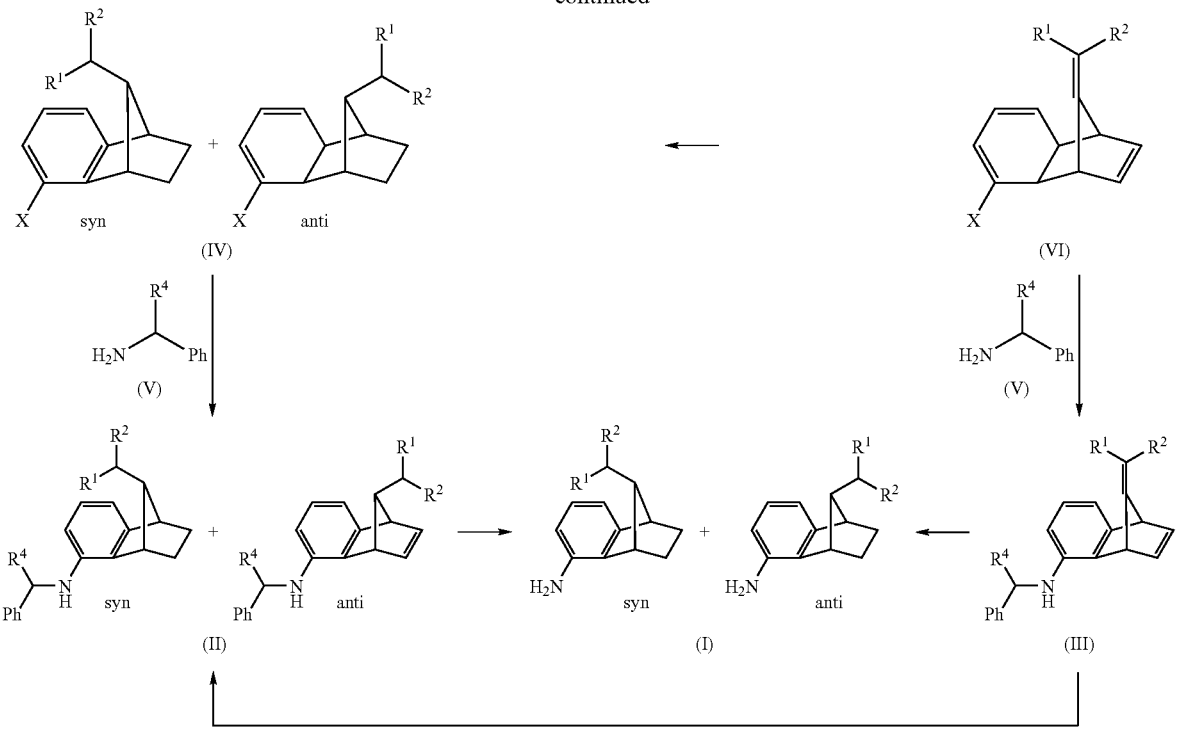

As already discussed above, the invention includes, in separate aspects:

(1) the formation of (I) from (II) or (III),
(2) the formation of (II) from (IV),
(3) the formation of (III) from (VI),
(4) the formation of (II) from (III),
(5) the formation of (IV) from (VI),
(6) the formation of (VI) from (VII), and
(7) the formation of (VII) from (IX) or (X).

The invention further includes the following multi-step processes which involve:

(8) the formation of (I) from (IV) via (II),
(9) the formation of (I) from (VI) via (III),
(10) the formation of (I) from (VI) via (IV) and (II),
(11) the formation of (I) from (VI) via (III) and (II),
(12) the formation of (VI) from (IX) or (X) via (VII),
(13) the formation of (I) from (IX) or (X) via (VI) and (III),
(14) the formation of (I) from (IX) or (X) via (VI), (IV) and (II), and
(15) the formation of (I) from (IX) or (X) via (VI), (III) and (II).

Thus according to still yet another aspect of the invention there is provided a process for the preparation of a compound of the general formula (I):

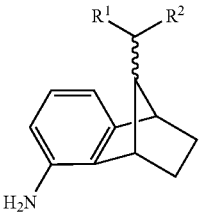

(I)

wherein $R^1$ and $R^2$ are independently H or $C_{1-6}$ alkyl, which comprises the steps of (a) reacting a compound of the general formula (IV):

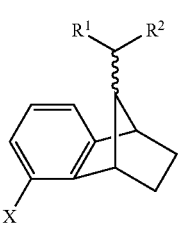

(IV)

wherein $R^1$ and $R^2$ have the meanings given above and X is chloro or bromo, with a benzylamine of the general formula (V):

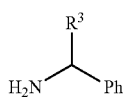
(V)

wherein $R^3$ is H or $C_{1-4}$ alkyl and Ph is phenyl, in the presence of a base and a catalytic amount of at least one palladium complex to form a compound of the general formula (II):

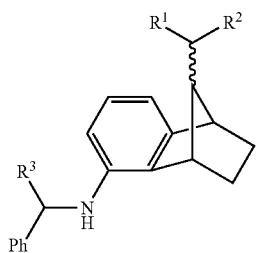
(II)

wherein $R^1$, $R^2$, $R^3$ and Ph have the meanings given above; and (b) treating the compound of the general formula (II) so formed with a reducing agent, the reducing agent being effective to cleave the benzyl moiety Ph-CH($R^3$)— from the benzylamino moiety PhCH($R^3$)NH— to leave an amino group.

In still yet another aspect of the invention there is provided a process for the preparation of a compound of the general formula (I):

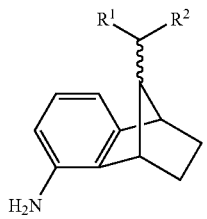
(I)

wherein $R^1$ and $R^2$ are independently H or $C_{1-6}$ alkyl, which comprises the steps of (a) reacting a compound of the general formula (VI):

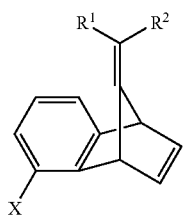
(VI)

wherein $R^1$ and $R^2$ have the meanings given above and X is chloro or bromo, with a benzylamine of the general formula (V):

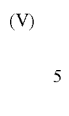
(V)

wherein $R^3$ is H or $C_{1-4}$ alkyl and Ph is phenyl, in the presence of a base and a catalytic amount of at least one palladium complex to form a compound of the general formula (III):

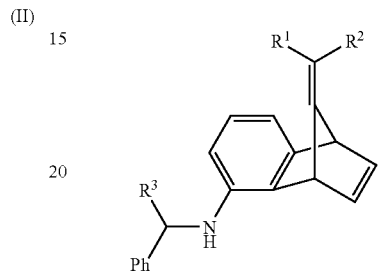
(III)

wherein $R^1$, $R^2$, $R^3$ and Ph have the meanings given above; and (b) treating the compound of the general formula (III) so formed with a reducing agent, the reducing agent being effective to cleave the benzyl moiety Ph-CH($R^3$)— from the benzylamino moiety PhCH($R^3$)NH— to leave an amino group and to reduce both the 2,3-double bond and the double bond joining the $R^1R^2C$— moiety to the 9-position of the benzonorbornene ring to single bonds.

In still yet another aspect of the invention there is provided a process for the preparation of a compound of the general formula (I):

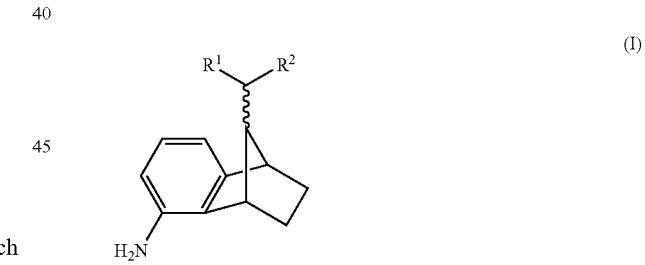
(I)

wherein $R^1$ and $R^2$ are independently H or $C_{1-6}$ alkyl, which comprises the steps of (a) treating a compound of the general formula (VI):

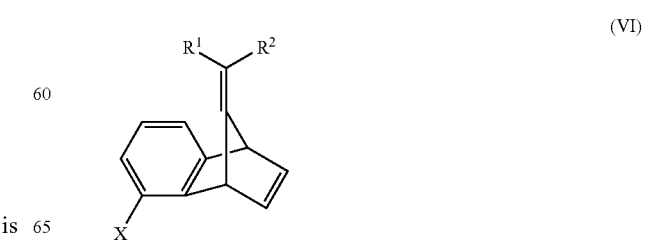
(VI)

wherein R¹ and R² have the meanings given above and X is chloro or bromo, with a reducing agent, the reducing agent being effective to reduce both the 2,3-double bond and the double bond joining the R¹R²C— moiety to the 9-position of the benzonorbornene ring to single bonds to form a compound of the general formula (IV):

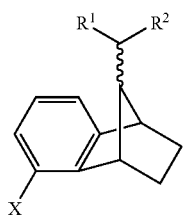

(IV)

wherein R¹, R² and X have the meanings given above;

(b) reacting the compound of the general formula (IV) so formed with a benzylamine of the general formula (V):

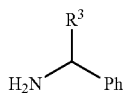

(V)

wherein R³ is H or $C_{1-4}$ alkyl and Ph is phenyl, in the presence of a base and a catalytic amount of at least one palladium complex to form a compound of the general formula (II):

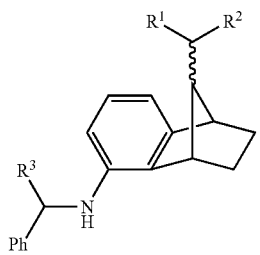

(II)

wherein R¹, R², R³ and Ph have the meanings given above; and (c) treating the compound of the general formula (II) so formed with a reducing agent, the reducing agent being effective to cleave the benzyl moiety Ph-CH(R³)— from the benzylamino moiety PhCH(R³)NH— to leave an amino group.

In still yet another aspect of the invention there is provided a process for the preparation of a compound of the general formula (I):

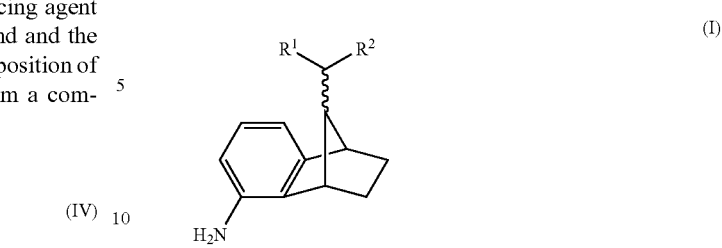

(I)

wherein R¹ and R² are independently H or $C_{1-6}$ alkyl, which comprises the steps of (a) reacting a compound of the general formula (VI):

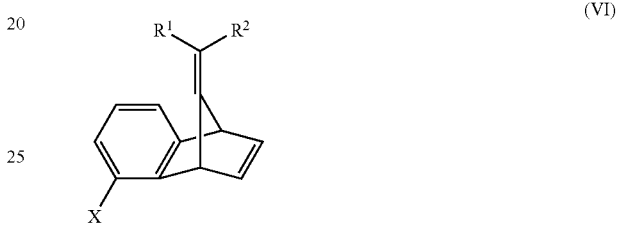

(VI)

wherein R¹ and R² have the meanings given above and X is chloro or bromo, with a benzylamine of the general formula (V):

(V)

wherein R³ is H or $C_{1-4}$ alkyl and Ph is phenyl, in the presence of a base and a catalytic amount of at least one palladium complex to form a compound of the general formula (III):

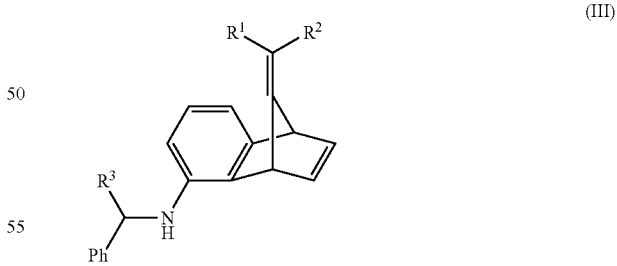

(III)

wherein R¹, R², R³ and Ph have the meanings given above;

(b) treating the compound of the general formula (III) so formed with a reducing agent, the reducing agent being effective to reduce both the 2,3-double bond and the double bond joining the R¹R²C— moiety to the 9-position of the benzonorbornene ring to single bonds but to leave the PhCH(R³)NH— moiety intact to form a compound of the general formula (II):

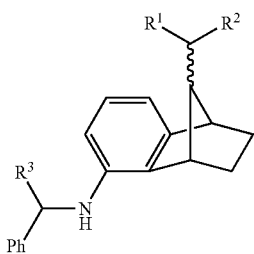

wherein $R^1$, $R^2$, $R^3$ and Ph have the meanings given above; and (c) treating the compound of the general formula (II) so formed with a reducing agent, the reducing agent being effective to cleave the benzyl moiety Ph-CH($R^3$)— from the benzylamino moiety PhCH($R^3$)NH— to leave an amino group.

In still yet another aspect of the invention there is provided a process for the preparation of a compound of the general formula (VI):

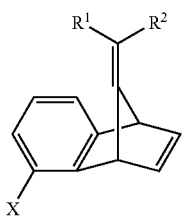

wherein $R^1$ and $R^2$ are independently H or $C_{1-6}$ alkyl and X is chloro or bromo, which comprises reacting a 1,2,3-trihalobenzene of the formula (IX) or (X):

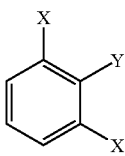

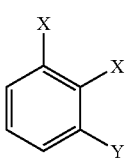

wherein X is chloro or bromo and Y is bromo or iodo, with an organometallic species such as a $C_{1-6}$ alkyl- or phenyllithium or a $C_{1-6}$ alkyl- or phenylmagnesium halide in the presence of a fulvene of the general formula (VIII):

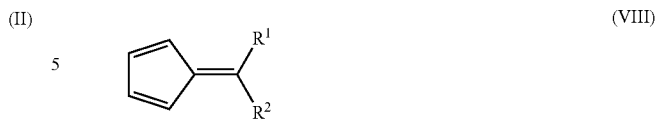

wherein $R^1$ and $R^2$ have the meanings given above, in an inert organic solvent and in an inert atmosphere.

In still yet another aspect of the invention there is provided a process for the preparation of a compound of the general formula (I):

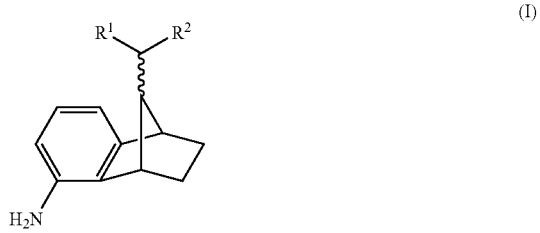

wherein $R^1$ and $R^2$ are independently H or $C_{1-6}$ alkyl, which comprises the steps of (a) reacting a 1,2,3-trihalobenzene of the formula (IX) or (X):

wherein X is chloro or bromo and Y is bromo or iodo, with an organometallic species such as a $C_{1-6}$ alkyl- or phenyllithium or a $C_{1-6}$ alkyl- or phenylmagnesium halide in an inert atmosphere to form a halobenzyne of the general formula (VII):

wherein X is chloro or bromo;

(b) reacting the halobenzyne of the general formula (VII) so formed with a fulvene of the general formula (VIII):

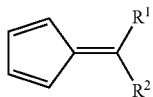
(VIII)

wherein $R^1$ and $R^2$ have the meanings given above, in an inert organic solvent to form a compound of the general formula (VI):

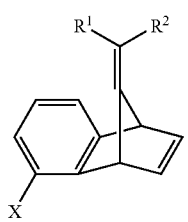
(VI)

wherein $R^1$ and $R^2$ have the meanings given above and X is chloro or bromo;

(c) reacting the compound of the general formula (VI) so formed with a benzylamine of the general formula (V):

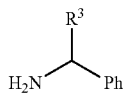
(V)

wherein $R^3$ is H or $C_{1-4}$ alkyl and Ph is phenyl, in the presence of a base and a catalytic amount of at least one palladium complex to form a compound of the general formula (III):

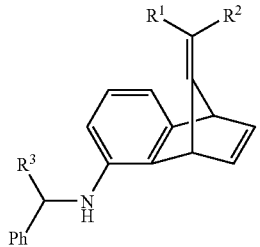
(III)

wherein $R^1$, $R^2$, $R^3$ and Ph have the meanings given above; and (d) treating the compound of the general formula (III) so formed with a reducing agent, the reducing agent being effective to cleave the benzyl moiety Ph-CH($R^3$)— from the benzylamino moiety PhCH($R^3$)NH— to leave an amino group and to reduce both the 2,3-double bond and the double bond joining the $R^1R^2C$— moiety to the 9-position of the benzonorbornene ring to single bonds.

In still yet another aspect of the invention there is provided a process for the preparation of a compound of the general formula (I):

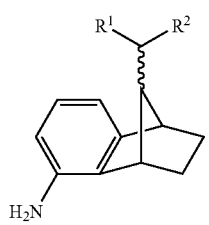
(I)

wherein $R^1$ and $R^2$ are independently H or $C_{1-6}$ alkyl, which comprises the steps of (a) reacting a 1,2,3-trihalobenzene of the formula (IX) or (X):

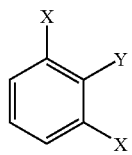
(IX)

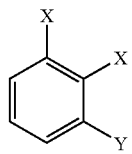
(X)

wherein X is chloro or bromo and Y is bromo or iodo, with an organometallic species such as a $C_{1-6}$ alkyl- or phenyllithium or a $C_{1-6}$ alkyl- or phenylmagnesium halide in an inert atmosphere to form a halobenzyne of the general formula (VII):

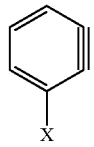
(VII)

wherein X is chloro or bromo;

(b) reacting the halobenzyne of the general formula (VII) so formed with a fulvene of the general formula (VIII):

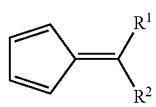
(VIII)

wherein $R^1$ and $R^2$ have the meanings given above, in an inert organic solvent to form a compound of the general formula (VI):

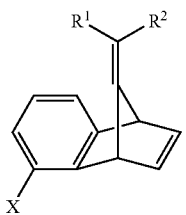

(VI)

wherein R¹ and R² have the meanings given above and X is chloro or bromo;

(c) treating a compound of the general formula (VI) so formed with a reducing agent, the reducing agent being effective to reduce both the 2,3-double bond and the double bond joining the R¹R²C— moiety to the 9-position of the benzonorbornene ring to single bonds to form a compound of the general formula (IV):

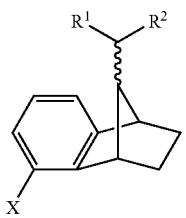

(IV)

wherein R¹, R² and X have the meanings given above;

(d) reacting the compound of the general formula (IV) so formed with a benzylamine of the general formula (V):

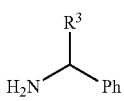

(V)

wherein R³ is H or $C_{1-4}$ alkyl and Ph is phenyl, in the presence of a base and a catalytic amount of at least one palladium complex to form a compound of the general formula (II):

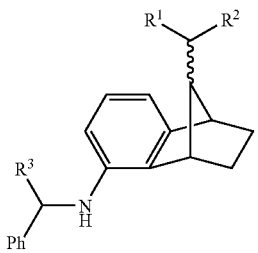

(II)

wherein R¹, R², R³ and Ph have the meanings given above; and (e) treating the compound of the general formula (II) so formed with a reducing agent, the reducing agent being effective to cleave the benzyl moiety Ph-CH(R³)— from the benzylamino moiety PhCH(R³)NH— to leave an amino group.

In still yet another aspect of the invention there is provided a process for the preparation of a compound of the general formula (I):

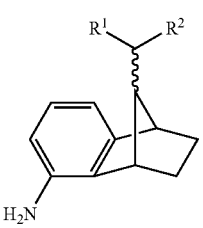

(I)

wherein R¹ and R² are independently H or $C_{1-6}$ alkyl, which comprises the steps of (a) reacting a 1,2,3-trihalobenzene of the formula (IX) or (X):

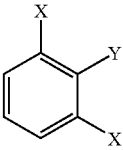

(IX)

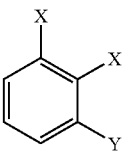

(X)

wherein X is chloro or bromo and Y is bromo or iodo, with an organometallic species such as a $C_{1-6}$ alkyl- or phenyllithium or a $C_{1-6}$ alkyl- or a phenylmagnesium halide in an inert atmosphere to form a halobenzyne of the general formula (VII):

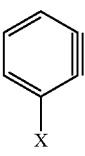

(VII)

wherein X is chloro or bromo;

(b) reacting the halobenzyne of the general formula (VII) so formed with a fulvene of the general formula (VIII):

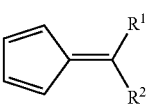

(VIII)

wherein R¹ and R² have the meanings given above, in an inert organic solvent to form a compound of the general formula (VI):

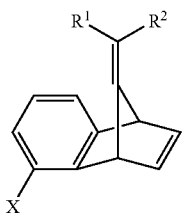

(VI)

wherein $R^1$ and $R^2$ have the meanings given above and X is chloro or bromo;

(c) reacting the compound of the general formula (VI) so formed with a benzylamine of the general formula (V):

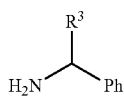

(V)

wherein $R^3$ is H or $C_{1-4}$ alkyl and Ph is phenyl, in the presence of a base and a catalytic amount of at least one palladium complex to form a compound of the general formula (III):

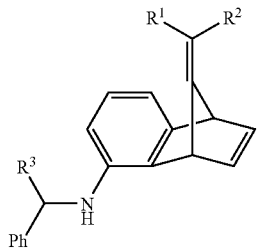

(III)

wherein $R^1$, $R^2$, $R^3$ and Ph have the meanings given above;

(d) treating the compound of the general formula (III) so formed with a reducing agent, the reducing agent being effective to reduce both the 2,3-double bond and the double bond joining the $R^1R^2C$— moiety to the 9-position of the benzonorbornene ring to single bonds but to leave the PhCH($R^3$)NH— moiety intact to form a compound of the general formula (II):

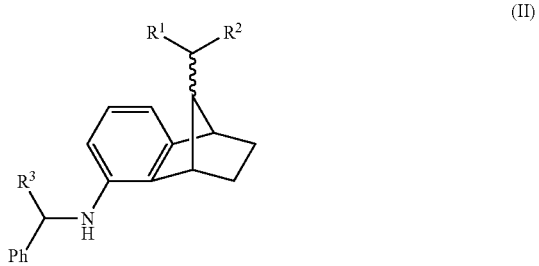

(II)

wherein $R^1$, $R^2$, $R^3$ and Ph have the meanings given above; and (e) treating the compound of the general formula (II) so formed with a reducing agent, the reducing agent being effective to cleave the benzyl moiety Ph-CH($R^3$)— from the benzylamino moiety PhCH($R^3$)NH— to leave an amino group.

Illustrative of the compounds of the general formula (I) that may be prepared by the process of the invention are the compounds listed in Table 1 below.

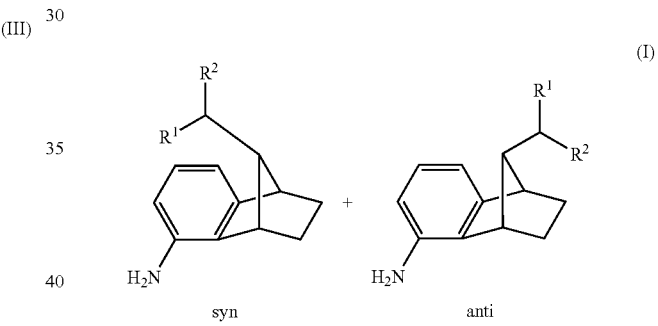

(I)

In Table 1, the values of $R^1$ and $R^2$ are given together with characterising data.

TABLE 1

| Compound No. | $R^1$ | $R^2$ | Melting point (° C.) & syn/anti ratio (by glc) | $^1$H-NMR proton shifts δ (ppm) (CDCl$_3$) |
|---|---|---|---|---|
| 1.01 | H | H | | |
| 1.02 | H | CH$_3$ | | |
| 1.03 | H | C$_2$H$_5$ | | |
| 1.04 | H | n-C$_3$H$_7$ | | |
| 1.05 | H | i-C$_3$H$_7$ | | |
| 1.06 | H | n-C$_4$H$_9$ | | |
| 1.07 | H | t-C$_4$H$_9$ | | |
| 1.08 | H | i-C$_4$H$_9$ | | |
| 1.09 | H | sec-C$_4$H$_9$ | | |
| 1.10 | H | n-C$_5$H$_{11}$ | | |
| 1.11 | H | n-C$_6$H$_{13}$ | | |
| 1.12 | CH$_3$ | CH$_3$ | m.p. 54-56; syn/anti-ratio 98:02 | $^1$H (syn-component): 6.91 (t, 1H), 6.64 (d, 1H), 6.48 (d, 1H), 3.54 (brd, exchangeable with D$_2$O, 2H), 3.20 (m, 1H), 3.15 (m, 1H), 1.91 (m, 2H), 1.53 (d, 1H), 1.18 (m, 2H), |

TABLE 1-continued

| Compound No. | $R^1$ | $R^2$ | Melting point (° C.) & syn/anti ratio (by glc) | $^1$H-NMR proton shifts δ (ppm) (CDCl$_3$) |
|---|---|---|---|---|
| | | | | 1.02 (m, 1H), 0.81 (d, 6H). $^{13}$C (syn-component): 147.73, 140.03, 130.15, 126.41, 113.35, 112.68, 69.00, 46.62, 42.06, 27.74, 26.83, 25.45, 22.32, 22.04. $^1$H (anti-component): 6.89 (t, 1H), 6.63 (d, 1H,) 6.46 (d, 1H), 3.55 (brd, exchangeable with D$_2$O, 2H), 3.16 (m, 1H), 3.13 (m, 1H), 1.87 (m, 2H), 1.48 (d, 1H), 1.42 (m, 1H), 1.12 (m, 2H), 0.90 (d, 6H). $^{13}$C (syn-component): 150.72, 138.74, 133.63, 126.15, 112.94, 111.53, 68.05, 45.21, 40.61, 26.25, 24.47, 23.55, 20.91 (2x). |
| 1.12 | CH$_3$ | CH$_3$ | viscous oil syn/anti-ratio 75:25 | |
| 1.13 | CH$_3$ | C$_2$H$_5$ | | |
| 1.14 | C$_2$H$_5$ | C$_2$H$_5$ | | |

The intermediate chemicals of the general formulae (II), (III), (IV) and (VI) are novel compounds and form still yet a further aspect of the present invention.

Thus, the invention also provides a compound of the general formula (II):

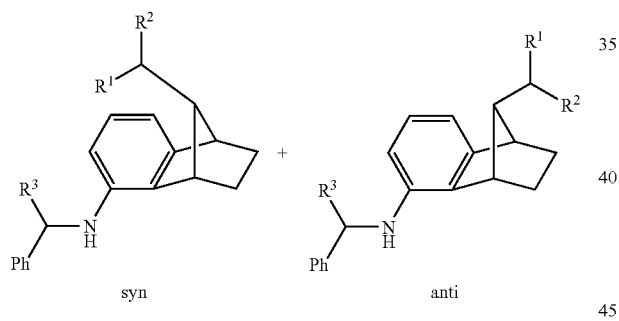

(II)

wherein $R^1$ and $R^2$ are independently H or C$_{1-6}$ alkyl, $R^3$ is H or C$_{1-4}$ alkyl and Ph is phenyl. Of particular interest are compounds (II) where $R^1$ and $R^2$ are selected from H, methyl and ethyl, and especially those where $R^1$ and $R^2$ are both methyl. Preferably $R^3$ is H. Illustrative of the compounds of formula (II) are the compounds listed in Table 2 below. In Table 2, $R^3$ is H, Ph is phenyl and the values of $R^1$ and $R^2$ are given together with characterising data.

TABLE 2

| Compound No. | $R^1$ | $R^2$ | Melting point (° C.) & syn/anti ratio (by glc) | $^1$H-NMR proton shifts δ (ppm) (CDCl$_3$) |
|---|---|---|---|---|
| 2.01 | H | H | | |
| 2.02 | H | CH$_3$ | | |
| 2.03 | H | C$_2$H$_5$ | | |
| 2.04 | H | n-C$_3$H$_7$ | | |

TABLE 2-continued

| Compound No. | R$^1$ | R$^2$ | Melting point (° C.) & syn/anti ratio (by glc) | $^1$H-NMR proton shifts δ (ppm) (CDCl$_3$) |
|---|---|---|---|---|
| 2.05 | H | i-C$_3$H$_7$ | | |
| 2.06 | H | n-C$_4$H$_9$ | | |
| 2.07 | H | t-C$_4$H$_9$ | | |
| 2.08 | H | i-C$_4$H$_9$ | | |
| 2.09 | H | sec-C$_4$H$_9$ | | |
| 2.10 | H | n-C$_5$H$_{11}$ | | |
| 2.11 | H | n-C$_6$H$_{13}$ | | |
| 2.12 | CH$_3$ | CH$_3$ | m.p. 87-90; syn/anti ratio 91:9 | $^1$H: 7.39-7.28 (m, 5H, syn + anti), 6.97 (t, 1H, syn + anti), 6.63 (d, 1H, syn + anti), 6.48 (d, 1H, syn + anti), 4.38 (dd, 2H, syn + anti), 3.84 (brd, exchangeable with D$_2$O, 1H, syn + anti), 3.19-3.14 (m, 2H, syn + anti), 1.94-1.90 (m, 2H, syn + anti), 1.53 (dt, J$_d$ = 10 Hz, 1H, syn), ca. 1.43 (m, 1H, anti), 1.20-1.16 (m, 2H, syn + anti), 1..06 (m, 1H, syn), 0.92-0.90 (2d, 6H, anti), 0.82 and 0.81 (2d, 6H, syn). |
| 2.13 | CH$_3$ | C$_2$H$_5$ | | |
| 2.14 | C$_2$H$_5$ | C$_2$H$_5$ | | |

The invention further provides a compound of the general formula (III):

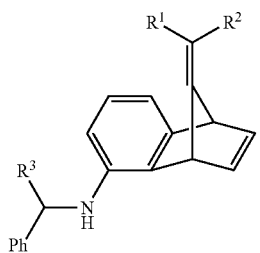

(III)

wherein R$^1$ and R$^2$ are independently H or C$_{1-6}$ alkyl, R$^2$ is H or C$_{1-4}$ alkyl and Ph is phenyl. Of particular interest are compounds (III) where R$^1$ and R$^2$ are selected from H, methyl and ethyl, and especially those where R$^1$ and R$^2$ are both methyl. Preferably R$^3$ is H. Where R$^1$ and R$^2$ are different, compound (III) may exist as the E- or Z-enantiomer or as a mixture of both in any proportion. The invention includes the separate enantiomers and any mixtures thereof.

Illustrative of the compounds of formula (IEi) are the compounds listed in Table 3 below. In Table 3, R$^3$ is H, Ph is phenyl and the values of R$^1$ and R$^2$ are given together with characterising data.

TABLE 3

| Compound No. | R$^1$ | R$^2$ | Melting point (° C.) | $^1$H-NMR proton shifts δ (ppm) (CDCl$_3$) |
|---|---|---|---|---|
| 3.01 | H | H | | |
| 3.02* | H | CH$_3$ | | |
| 3.03* | H | C$_2$H$_5$ | | |
| 3.04* | H | n-C$_3$H$_7$ | | |
| 3.05* | H | i-C$_3$H$_7$ | | |
| 3.06* | H | n-C$_4$H$_9$ | | |
| 3.07* | H | t-C$_4$H$_9$ | | |
| 3.08* | H | i-C$_4$H$_9$ | | |
| 3.09* | H | sec-C$_4$H$_9$ | | |
| 3.10* | H | n-C$_5$H$_{11}$ | | |
| 3.11* | H | n-C$_6$H$_{13}$ | | |
| 3.12 | CH$_3$ | CH$_3$ | m.p. 98-100 | $^1$H: 7.42-7.24 (m, 5H), 6.93 (m, 2H), 6.86 (t, 1H), 6.77 (d, 1H), 6.38 (d, 1H), 4.39 (m, 1H), 4.36 (m, 1H), 4.38 (s, 2H), 3.8 (brd, exchangeable with D$_2$O, 1H), 1.55 (s, 3H), 1.54 (s, 3 > H). |
| 3.13* | CH$_3$ | C$_2$H$_5$ | | |
| 3.14 | C$_2$H$_5$ | C$_2$H$_5$ | | |

*indicates E/Z-mixtures

The invention further provides a compound of the general formula (IV):

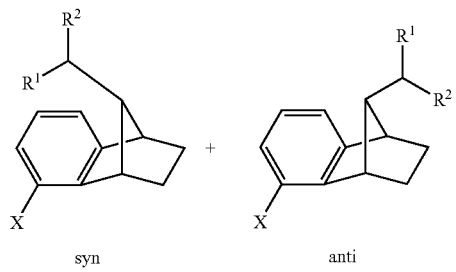

syn     anti wherein $R^1$ and $R^2$ are independently H or $C_{1-6}$ alkyl and X is chloro or bromo. Of particular interest are compounds (II) where $R^1$ and $R^2$ are selected from H, methyl and ethyl, and especially those where $R^1$ and $R^2$ are both methyl. Preferably X is chloro.

Illustrative of the compounds of formula (IV) are the compounds listed in Table 4 below. In Table 4, the values of $R^1$, $R^2$ and X are given together with characterising data.

TABLE 4

| Compound No. | X | $R^1$ | $R^2$ | Melting point (° C.) & syn/anti ratio (by glc) | $^1$H-NMR proton shifts δ (ppm) (CDCl$_3$) |
|---|---|---|---|---|---|
| 4.01 | Br | H | H | | |
| 4.02 | Br | H | $CH_3$ | | |
| 4.03 | Br | H | $C_2H_5$ | | |
| 4.04 | Br | H | n-$C_3H_7$ | | |
| 4.05 | Br | H | i-$C_3H_7$ | | |
| 4.06 | Br | H | n-$C_4H_9$ | | |
| 4.07 | Br | H | t-$C_4H_9$ | | |
| 4.08 | Br | H | i-$C_4H_9$ | | |
| 4.09 | Br | H | sec-$C_4H_9$ | | |
| 4.10 | Br | H | n-$C_5H_{11}$ | | |
| 4.11 | Br | H | n-$C_6H_{13}$ | | |
| 4.12 | Br | $CH_3$ | $CH_3$ | | |
| 4.13 | Br | $CH_3$ | $C_2H_5$ | | |
| 4.14 | Br | $C_2H_5$ | $C_2H_5$ | | |
| 4.15 | Cl | H | H | | |
| 4.16 | Cl | H | $CH_3$ | | |
| 4.17 | Cl | H | $C_2H_5$ | | |
| 4.18 | Cl | H | n-$C_3H_7$ | | |
| 4.19 | Cl | H | i-$C_3H_7$ | | |
| 4.20 | Cl | H | n-$C_4H_9$ | | |
| 4.21 | Cl | H | t-$C_4H_9$ | | |
| 4.22 | Cl | H | i-$C_4H_9$ | | |
| 4.23 | Cl | H | sec-$C_4H_9$ | | |
| 4.24 | Cl | H | n-$C_5H_{11}$ | | |
| 4.25 | Cl | H | n-$C_6H_{13}$ | | |
| 4.26 | Cl | $CH_3$ | $CH_3$ | m.p. 61-62; syn/anti-ratio 91:9 | $^1$H (syn component): 7.06 (d, 1H), 7.04 (d, 1H), 7.01 (t, 1H), 3.49 (m, 1H), 3.24 (m, 1H), 1.96-1.97 (m, 2H), 1.57 (dt, $J_d$ = 10 Hz, $J_t$ = 1.2 Hz, 1H), 1.16-1.22 (m, 2H), 0.93 (m, 1H), 0.83 (d, 3H), 0.81 (d, 3H). $^{13}$C (syn-component): 148.6, 143.8, 128.1, 127.0, 125.8, 119.8, 69.0, 47.1, 44.8, 27.4, 26.4, 25.5, 22.1, 22.0. $^1$H (anti-component): 7.03 (d, 1H), 7.00 (d, 1H), 6.97 (t, 1H), 3.43 (m, 1H), 3.21 (m, 1H), 1.97-1.92 (m, 2H), 1.51 (br.d, J = 10.8 Hz, 1H), 1.43 (m, 1H), 1.16-1.10 (m, 2H), 0.92 (d, 3H), 0.90 (d, 3H). $^{13}$C (anti-component): 151.4, 146.7, 126.8, 126.6, 125.5, 118.7, 67.9, 45.6, 43.4, 26.1, 24.2, 23.2, 20.9, 20.8. |
| 4.27 | Cl | $CH_3$ | $C_2H_5$ | | |
| 4.28 | Cl | $C_2H_5$ | $C_2H_5$ | | |

The invention further provides a compound of the general formula (VI):

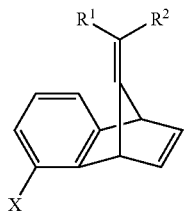

(VI)

wherein $R^1$ and $R^2$ are independently H or Clue alkyl and X is chloro or bromo. Of particular interest are compounds (VI) where $R^1$ and $R^2$ are selected from H, methyl and ethyl, and especially those where $R^1$ and $R^2$ are both methyl. Preferably X is chloro. Where $R^1$ and $R^2$ are different, compound (VI) may exist as the E- or Z-isomer or as a mixture of both in any proportion. The invention includes the separate enantiomers and any mixtures thereof. Illustrative of the compounds of formula (VI) are the compounds listed in Table 5 below. In Table 5, the values of $R^1$, $R^2$ and X are given together with characterising data.

The following non-limiting examples illustrate the invention in more detail.

EXAMPLE 1

Preparation of
5-Bromo-9-isopropylidene-benzonorbornadiene
(Compound No. 5.12)

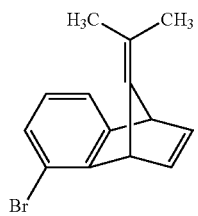

a) n-Butyllithium Variant, from
1,3-dibromo-2-iodo-benzene

To a stirred solution of 1,3-dibromo-2-iodo-benzene (5.00 g, 13.8 mmol) and 6,6-dimethylfulvene (7.57 g, assay 97%,

TABLE 5

| Compound No. | X | $R^1$ | $R^2$ | Melting point (° C.) | $^1$H-NMR proton shifts δ (ppm) (CDCl$_3$) |
|---|---|---|---|---|---|
| 5.01 | Br | H | H | | |
| 5.02* | Br | H | CH$_3$ | | |
| 5.03* | Br | H | C$_2$H$_5$ | | |
| 5.04* | Br | H | n-C$_3$H$_7$ | | |
| 5.05* | Br | H | i-C$_3$H$_7$ | | |
| 5.06* | Br | H | n-C$_4$H$_9$ | | |
| 5.07* | Br | H | t-C4H9 | | |
| 5.08* | Br | H | i-C$_4$H$_9$ | | |
| 5.09* | Br | H | sec-C$_4$H$_9$ | | |
| 5.10* | Br | H | n-C$_5$H$_{11}$ | | |
| 5.11* | Br | H | n-C$_6$H$_{13}$ | | |
| 5.12 | Br | CH$_3$ | CH$_3$ | 90-91 | $^1$H: 7.13 (d, 1H), 7.06 (d, 1H), 6.95 (m, 2H), 6.81 (t, 1H), 4.57 (m, 1H), 4.45 (m, 1H), 1.58 (s, 3H), 1.55 (s, 3H). $^{13}$C: 160.46, 152.91, 150.81, 143.26, 142.24, 127.68, 126.10, 119.44, 115.67, 103.73, 51.69, 51.16, 19.04, 18.90. |
| 5.13* | Br | CH$_3$ | C$_2$H$_5$ | | |
| 5.14 | Br | C$_2$H$_5$ | C$_2$H$_5$ | | |
| 5.15 | Cl | H | H | | |
| 5.16* | Cl | H | CH$_3$ | | |
| 5.17* | Cl | H | C$_2$H$_5$ | | |
| 5.18* | Cl | H | n-C$_3$H$_7$ | | |
| 5.19* | Cl | H | i-C$_3$H$_7$ | | |
| 5.20* | Cl | H | n-C$_4$H$_9$ | | |
| 5.21* | Cl | H | t-C$_4$H$_9$ | | |
| 5.22* | Cl | H | i-C$_4$H$_9$ | | |
| 5.23.* | Cl | H | sec-C$_4$H$_9$ | | |
| 5.24* | Cl | H | n-C$_5$H$_{11}$ | | |
| 5.25* | Cl | H | n-C$_6$H$_{13}$ | | |
| 5.26 | Cl | CH$_3$ | CH$_3$ | 83-85 | $^1$H: 7.10 (d, 1H), 6.94 (m, 2H), 6.93-6.85 (m, 2H), 4.63 (m, 1H), 4.41 (m, 1H), 1.57 (s, 3H), 1.55 (s, 3H). $^{13}$C: 160.55, 152.84, 148.35, 143.23, 142.21, 126.90, 125.77, 124.90, 118.92, 103.57, 51.35, 49.11, 19.00, 18.89. |
| 5.27* | Cl | CH$_3$ | C$_2$H$_5$ | | |
| 5.28 | Cl | C$_2$H$_5$ | C$_2$H$_5$ | | |

*indicates E/Z-mixtures 69 mmol) in dry toluene (60 ml) under a nitrogen atmosphere 5.5 ml of a 2.5M toluene solution of n-butyllithium (14.5 mmol) were added dropwise at 0° C. within 10 minutes. After a further 10 minutes at 0° C. and 1 hour at ambient temperature, the reaction mixture was poured onto a saturated aqueous solution of ammonium chloride, extracted with ethyl acetate, washed with brine and water, dried over sodium sulphate and evaporated. Purification of the crude material on silica gel in hexane afforded 2.55 g of the desired product as a yellow oil (assay 99% by g.l.c., 70% yield). Yellow crystals of m.p. 90-91° C. were obtained from cold hexane.

b) n-Butyllithium Variant, from 1,2,3-tribromo-benzene

To a stirred solution of 1,2,3-tribromo-benzene (4.34 g, 13.8 mmol) and 6,6-dimethylfulvene (2.38 g, assay 92.6%, 20.7 mmol) in dry toluene (60 ml) under a nitrogen atmosphere, 5.5 ml of a 2.5M toluene solution of n-butyllithium (14.5 mmol) were added dropwise at −5 to 0° C. within 10 minutes. After a further 10 minutes at 0° C. and 2 hours at ambient temperature, the reaction mixture was poured onto a saturated aqueous solution of ammonium chloride, extracted with ethyl acetate, washed with brine and water, dried over sodium sulphate and evaporated. Purification of the crude material on silica gel in hexane afforded 2.38 g of the desired product as a yellow oil (assay 84% by g.l.c., 55% yield).

c) Isopropylmagnesium Chloride Variant, from 1,3-dibromo-2-iodo-benzene

A solution of 1,3-dibromo-2-iodo-benzene (45.95 g, 0.124 mol) in dry toluene (200 ml) under a nitrogen atmosphere was reacted at −8 to −15° C. with 2M isopropylmagnesium chloride in tetrahydrofuran (63.5 ml, 0.124 mol) for 1 hour. Subsequent addition of 6,6-dimethylfulvene (16.54 g, assay 97.8%, 0.15 mol) at 0° C. was followed by heating to reflux temperature for 19 hours. The reaction mixture was poured onto a saturated aqueous solution of ammonium chloride, extracted with ethyl acetate, washed with brine and water, dried over sodium sulphate and evaporated. Chromatography of the crude material on silica gel in hexane gave the desired product (27.84 g, assay 79% by g.l.c., 66% yield).

EXAMPLE 2

Preparation of 5-chloro-9-isopropylidene-benzonorbornadiene (Compound No. 5.26)

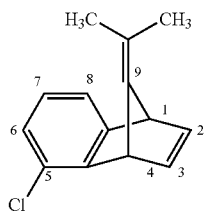

a) n-Butyllithium Variant, from 1,3-dichloro-2-iodo-benzene

To a stirred solution of 1,3-dichloro-2-iodo-benzene (38.21 g, 140 mmol) and 6,6-dimethyl-fulvene (46.35 g, assay 96.2%, 420 mmol) in dry toluene (600 ml) under a nitrogen atmosphere, 58.8 ml of a 2.5M toluene solution of n-butyllithium (147 mmol) were added dropwise at 0° C. within 16 minutes. After a further 10 minutes at 0° C., the reaction mixture was allowed to stand at ambient temperature overnight. Aqueous work up with saturated aqueous ammonium chloride and ethyl acetate extraction followed by washings with brine and water and drying over sodium sulphate gave a crude material which was purified by chromatography on silica gel in hexane to give 19.79 g of the desired product as a yellow oil (assay 94.7% by g.l.c., 62% yield). Yellow crystals of m.p. 83-85° C. were obtained from cold hexane.

b) Isopropylmagnesium Chloride Variant, from 2-bromo-1,3-dichloro-benzene

A solution of 2-bromo-1,3-dichlorobenzene (22.59 g, 0.1 mol) in dry toluene (100 ml) under a nitrogen atmosphere was reacted at −8 to −15° C. with 2M isopropylmagnesium chloride in tetrahydrofuran (50 ml, 0.1 mol) for 1 hour. Subsequent addition of 6,6-dimethylfulvene (13.03 g, assay 97.8%, 0.12 mol) at 0° C. was followed by heating to reflux temperature for 10 hours. Aqueous work up with saturated aqueous ammonium chloride and ethyl acetate extraction followed by washings with brine and water and drying over sodium sulphate gave the crude material which was purified by chromatography on silica gel in hexane to give the desired product (19.03 g, assay 95.2% by g.l.c., 83.6% yield) as a yellow solid.

c) Isopropylmagnesium Chloride Variant, from 1,3-dichloro-2-iodo-benzene

A solution of 1,3-dichloro-2-iodo-benzene (2.39 g, 8.76 mmol) in dry toluene (10 ml) under a nitrogen atmosphere was reacted at −8 to −15° C. with 2M isopropylmagnesium chloride in tetrahydrofuran (4.4 ml, 8.76 mmol) for 1 hour. Subsequent addition of 6,6-dimethylfulvene (1.45 g, assay 96.2%, 13.15 mmol) at 0° C. was followed by heating to reflux temperature for 22 hours. Aqueous work up with saturated aqueous ammonium chloride and ethyl acetate extraction followed by washings with brine and water and drying over sodium sulphate gave the crude material which was purified by chromatography on silica gel in hexane to give the desired product (1.75 g, assay 86.4% by g.l.c., 79.5% yield) as a yellow solid.

d) Isopropylmagnesium Chloride Variant, from 1-bromo-2,3-dichloro-benzene

A solution of 1-bromo-2,3-dichloro-benzene (22.59 g, 0.1 mol) in dry toluene (100 ml) under a nitrogen atmosphere was reacted at −8 to −15° C. with 2M isopropylmagnesium chloride in tetrahydrofuran (50 ml, 0.1 mol) for 1 hour. Subsequent addition of 6,6-dimethylfulvene (16.56 g, assay 96.2%, 0.15 mol) at 0° C. was followed by heating to reflux temperature for 10 hours. Aqueous work up with saturated aqueous ammonium chloride and ethyl acetate extraction followed by washings with brine and water and drying over sodium sulphate gave the crude material which was purified by chromatography on silica gel in hexane to give the desired product (19.57 g, assay 84.4% by g.l.c., 76.2% yield) as a yellow solid.

e) Isopropylmagnesium Chloride Variant, from 1-bromo-2,3-dichloro-benzene

A solution of 1-bromo-2,3-dichloro-benzene (37.6 g, 0.165 mol) in THF (170 ml) was added to 2M isopropylmagnesium chloride in tetrahydrofuran (10 g, 0.206 mol) under a nitrogen atmosphere at −10° C. and reaction mixture was stirred over 1 hour. This Grignard intermediate was added over 4 hours to a solution of 6,6-dimethylfulvene (19.9 g, 0.173 mol) in toluene at 85° C. The reaction mixture was stirred over one hour to complete the conversion of the reaction. Reaction was quenched with saturated aqueous ammonium chloride and phases were separated. Evaporation of THF/Toluene afforded the desired compound No. 5.26 (39.2 g, 80.5% yield) as a yellow solid.

EXAMPLE 3

Preparation of 5-chloro-9-isopropyl-benzonorbornene (Syn/Anti-Mixture, Syn-Enriched) (Compound. No. 4.26)

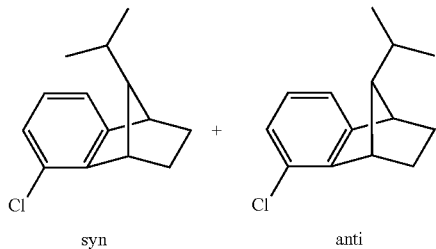

5-Chloro-9-isopropylidene-benzonorbornadiene (30.0 g, 0.1384 mol, prepared as described in Example 2) was hydrogenated at 20 to 25° C. and at ambient pressure in methanol (300 ml) in the presence of 5% Rh/C (6 g). Hydrogen up-take was 97% after 2 hours. Filtration and evaporation was followed by purification on silica gel in hexane to give the desired product (29.05 g, 95% yield) as a colourless solid, m.p. 61-62° C. The syn/anti ratio was determined by g.l.c. as 91:9.

EXAMPLE 4

Preparation of N-benzyl-5-amino-5-isopropyl-benzonorbornene (Syn/Anti-Mixture, Syn-Enriched; Compound. No. 2.12)

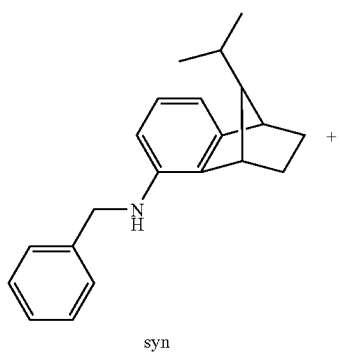

syn

-continued

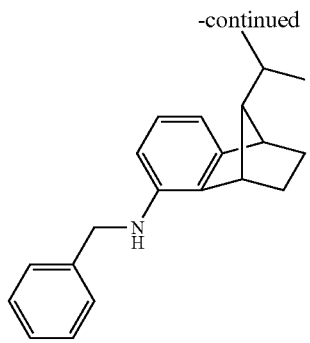

anti a) From 5-chloro-9-isopropyl-benzonorbornene (syn-enriched 91.9; Compound No. 4.26)

aa) Using R(−)-di-tert.-butyl-[1-[(S)-2-(dicyclohexylphosphanyl)-ferrocenyl]ethyl]phosphine as a Ligand i) (S/C 100, 1 mol %)

To a mixture of 5-chloro-9-isopropyl-benzonorbornene [syn-enriched 91:9; Compound No. 4.26, prepared as described in Example 3] (1.0 g, 4.53 mmol), sodium tert-butoxide (719 mg, assay 97%, 7.25 mmol), palladium acetate (10.2 mg, 0.045 mmol) and R(−)-di-tert-butyl-[1-[(S)-2-(dicyclohexylphosphanyl)-ferrocenyl]ethyl]phosphine (25.1 mg, 0.045 mmol) in a Schlenk tube under argon, dimethoxyethane (30 ml) and benzylamine (0.728 g, 6.8 mmol) were added. The mixture was heated under efficient stirring to 105° C. for 21 hours. After filtration on Hyflo® the reaction mixture was poured into water (30 ml), extracted with ether, washed with brine and water and dried over sodium sulphate to give the crude material. Purification on silica gel in ethyl acetate/hexane (1:9) afforded the desired product (1.33 g, assay 92%, 92% yield) as an orange oil. The syn/anti ratio was 91:9 (by g.l.c.). Colourless crystals were obtained from hexane, m.p. 87-90° C.

ii) (S/C 200, 0.5 mol %)

The reaction described in (i) above was repeated with 0.005 equivalents of palladium acetate and 0.005 equivalents of the same phosphine ligand, giving the desired product in a yield of 79%.

ab) Using 1,3-bis-(2,6-diisopropylphenyl)-imidazolium chloride as a Ligand i) S/C 200, 0.5 mol % Catalyst To a mixture of 5-chloro-9-isopropyl-benzonorbornene [syn-enriched 91:9; Compound No. 4.26, prepared as described in Example 3] (5.0 g, 22.65 mmol), sodium tert-butoxide (3.591 g, assay 97%, 36.2 mmol), palladium acetate (25.4 mg, 0.113 mmol) and 1,3-bis-(2,6-diisopropylphenyl)-imidazolium chloride (48.1 mg, 0.113 mmol) in a Schlenk tube under argon, dimethoxyethane (150 ml) and benzylamine (3.641 g, 34 mmol) were added. The mixture was heated under efficient stirring to 105° C. for 19 hours. After filtration on Hyflo® the reaction mixture was poured into water, extracted with ether, washed with brine and water and dried over sodium sulphate to give the crude material (8.53 g). Purification on silica gel in ethyl acetate/hexane (1:9) afforded the desired product (6.28 g, assay 91%, 86% yield)

as an orange oil. The syn/anti ratio was 89:11 (by g.l.c.). Crystallisation from hexane proceeded with further syn-enrichment giving 3.04 g colourless crystals, m.p. 98-100° C. (syn/anti ratio 98.5:1.5)

b) From N-benzyl-5-amino-9-isopropylidene-benzonorbornadiene (Compound No. 3.12)

N-benzyl-5-amino-9-isopropylidene-benzonorbornadiene (Compound No 3.12, prepared as described in Example 5) (1.00 g, 3.479 mmol) dissolved in a mixture of tetrahydrofuran (15 ml) and methanol (15 ml) was hydrogenated in the presence of 5% Rh/C (400 mg) at ambient temperature and 4 bar during 24.5 hours giving the desired compound (0.39 g (38%); syn/anti ratio 98:2 (by g.l.c.)) as a crystalline solid (m.p. 89-92° C.) besides 5-amino-5-isopropyl-benzonorbornene (11%, syn/anti ratio 87:13 (by g.l.c.) (Compound No. 5.12) after purification on silica gel in ethyl acetate-hexane (1:9).

EXAMPLE 5

Preparation of N-benzyl-5-amino-9-isopropylidene-benzonorbornadiene (Compound No 3.12)

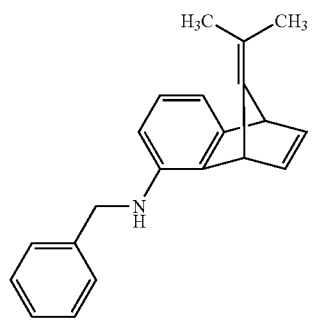

a) S/C 100 (1 mol % Catalyst)

To a mixture of 5-chloro-9-isopropylidene-benzonorbornadiene [Compound. No. 5.26 prepared as described in Example 2] (1.0 g, 4.61 mmol), sodium tert-butoxide (0.731 g, assay 97%, 7.38 mmol), palladium acetate (10.3 mg, 0.046 mmol) and 1,3-bis-(2,6-diisopropyl-phenyl)-imidazolium chloride (19.6 mg, 0.046 mmol) in a Schlenk tube under argon, diethylene glycol dimethyl ether (diglyme) (30 ml) and benzylamine (0.741 g, 6.91 mmol) were added. The mixture was heated under efficient stirring to 140-145° C. for 21 hours. After filtration on Hyflo® the reaction mixture was poured into water, extracted with ether, washed with brine and water and dried over sodium sulphate to give the crude material (9.54 g). Purification by chromatography on silica gel in ethyl acetate/hexane (1:9) afforded the desired product (1.54 g, assay 84%, 98% yield) as a yellow viscous oil.

b) S/C 400 (0.25 mol % Catalyst)

To a mixture of 5-chloro-9-isopropylidene-benzonorbornadiene [Compound. No. 5.26 prepared as described in Example 2] (5.0 g, 23.07 mmol), sodium tert-butoxide (3.548 g, assay 97%, 36.9 mmol), palladium acetate (12.9 mg, 0.0576 mmol) and 1,3-bis-(2,6-diiso-propylphenyl)-imidazolium chloride (24.5 mg, 0.0576 mmol) in a Schlenk tube under argon, diethylene glycol dimethyl ether (diglyme) (150 ml) and benzylamine (3.71 g, 34.6 mmol) were added. The mixture was heated under efficient stirring to 140-145° C. for 24 hours. After filtration on Hyflo® the reaction mixture was poured into water, extracted with ether, washed with brine and water and dried over sodium sulphate. Evaporation for 2 hours at 2 mbar and 75° C. gave the crude material (6.75 g). Purification on silica gel in ethyl acetate/hexane (1:9) afforded the desired product (6.27 g, assay 94%, 89% yield) as a yellow viscous oil.

c) Preparation of N-benzyl-5-amino-9-isopropylidene-benzonorbornadiene hydrochloride

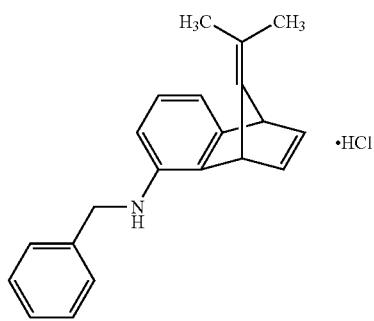

In an inert reactor, 5-chloro-9-isopropylidene-benzonorbornadiene [Compound. No. 5.26 prepared as described in Example 2] (27 g, 0.125 mol) was dissolved in xylene (125 g), and sodium tert-butoxide (15 g, 0.156 mol), palladium chloride (0.22 g, 0.0012 mol), 1,3-bis-(2,6-diisopropylphenyl)-imidazolium chloride (0.53 g, 0.0012 mol) and benzylamine (20.1 g, 0.187 mol) were added. The mixture was heated to 125° C. for 3 hours until completion of the reaction. Water was added to the reaction mixture and the pH wwas adjusted to 6 with HCl. Activated carbon was added, the suspension was clarified and phases were separated. Xylene was distilled off, replaced by hexane and a bleaching earth treatment was carried out. The product was isolated as HCl salt (18.5 g, assay 94% by HPLC., 43% yield)

EXAMPLE 6

Preparation of 5-amino-5-isopropyl-benzonorbornene (Syn/Anti-Mixture, Syn-Enriched) (Compound No. 1.12)

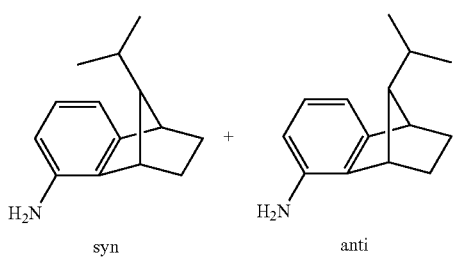

a) From N-benzyl-5-amino-5-isopropyl-benzonorbornene (Syn/Anti Ratio 97:3; Compound No. 2.12)

N-Benzyl-5-amino-5-isopropyl-benzonorbornene [syn/anti ratio 97:3; Compound No. 2.12 prepared as described in Example 4] (3.00 g, assay 97%, 9.98 mmol) dissolved in a mixture of methanol (30 ml) and tetrahydrofurane (20 ml), was hydrogenated at ambient pressure and temperature in the presence of 5% Pd/C (300 mg) over 20 hours. Filtration and evaporation of the solvent afforded the desired aniline as a solid (2.03 g, assay 98% by g.l.c., m.p. 54-56° C., 98% yield) with a syn/anti ratio of 98:2 (by g.l.c.).

b) From N-benzyl-5-amino-9-isopropylidene-benzonorbornadiene (Compound No 3.12)

N-Benzyl-5-amino-9-isopropylidene-benzonorbornadiene [Compound No. 3.12, prepared as described in Example 5] (1.00 g, 3.479 mmol) dissolved in a mixture of tetrahydrofuran (15 ml) and methanol (15 ml) was exhaustively hydrogenated in the presence of 5% Pd/C (400 mg) at ambient temperature and 4 bar during 24 hours giving after purification on silica gel in ethyl acetate-hexane (1:9) the desired aniline (0.61 g, 85%); syn/anti-ratio 74:24 (by g.l.c.) as a viscous oil.

Hydrogenation at ambient temperature and 40 bar at otherwise identical conditions gave the desired aniline (0.67 g, 96%) in a syn/anti ratio of 75:25.

Hydrogenation at atmospheric pressure under otherwise identical conditions afforded compound No 3.12 in a yield of 65% and a syn/anti-ratio of 61:39 (by g.l.c.).

In a preferred embodiment of the present invention, the reducing agent used in the process for the preparation of the compound of the general formula (I) from the compound of the general formula (III) is hydrogen in the presence of a palladium catalyst.

This preferred embodiment makes it possible to prepare in a simple manner compounds of formula (I) in which the ratio of the syn epimer of formula (Ia) to the anti epimer of formula (Ib) is significantly enriched; usually, a syn/anti ratio of more than 55:45 can be achieved; typically a syn/anti ratio of from 60:40 to 99:1 can be achieved. It is therefore a particular advantage of this preferred embodiment that mixtures of compounds of formula I can be prepared in simple manner that have a syn/anti ratio in favour of the syn epimer.

In this preferred embodiment of the process according to the invention, a compound of the general formula (III):

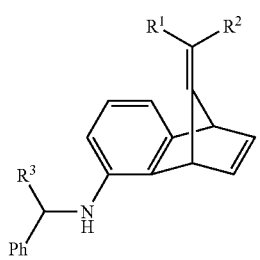

(III)

wherein $R^1$ and $R^2$ are independently H or $C_{1-6}$ alkyl, $R^3$ is H or $C_{1-4}$ alkyl and Ph is phenyl, is reacted with hydrogen in the presence of a palladium catalyst to form a compound of the general formula (I)

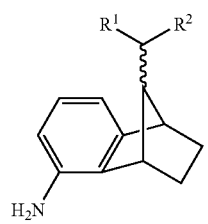

(I)

wherein $R^1$ and $R^2$ are independently H or $C_{1-6}$ alkyl, and wherein the ratio of the syn epimer of formula (Ia)

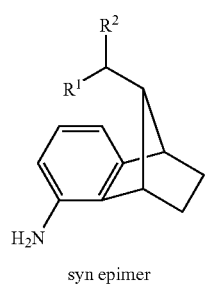

(Ia)

syn epimer wherein $R^1$ and $R^2$ are as defined for formula (I), to the anti epimer of formula (Ib)

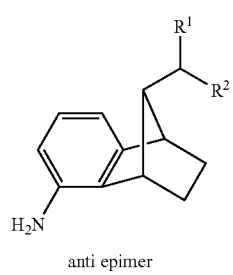

(Ib)

anti epimer wherein $R^1$ and $R^2$ are as defined for formula (I), is more than 55:45.

In a particular embodiment, compounds of formula (I) are prepared in which the ratio of the syn epimer of formula (Ia) to the anti epimer of formula (Ib) is from 75:25 to 95:5; preferably from 80:20 to 95:5; more preferably from 80:20 to 90:10.

Suitable palladium catalysts are, for example, heterogenous palladium catalysts, such as palladium on carbon, palladium on aluminium oxide, palladium on silica, palladium on barium carbonate, palladium on barium sulfate, palladium on calcium carbonate or homogenous palladium catalysts, such as palladium acetate, palladium chloride, palladium hydroxide or palladium oxide, or mixtures thereof. Special preference is given to palladium on carbon. Suitable heterogenous palladium catalysts have different water contents, suitable palladium catalysts can have a water content of up to 80% (w/w).

Suitable amounts of palladium catalyst are 0.01 to 10 mol % calculated on the basis of the compound of formula (III); preferred are 0.1 to 1 mol %.

The reaction is preferably carried out in the presence of an inert solvent. Suitable solvents are, for example, alcohols, such as methanol, ethanol, propanol or isopropanol, or aprotic solvents, such as tetrahydrofuran, tert-butyl methyl ether, ethyl acetate, dioxane or toluene, and mixtures thereof; special preference is given to ethanol or methanol.

The temperatures are generally from 0° C. to 80° C., with preference being given to a range from 0° C. to 45° C., more preferred is a range of 20° C. to 45° C., even more preferred is a range of 20° C. to 30° C.

The reaction time is generally from 1 to 100 hours, preferably from 1 to 24 hours.

Preferably the reaction is carried out at a pressure of at least 2 bar, more preferred is a pressure from 2 to 50 bar, even more preferred 5 to 50 bar. In one embodiment of the invention a pressure from 7 to 20 bar is used, preferably 7 to 15 bar, more preferably 8 to 12 bar.

In a special embodiment of this preferred embodiment of the invention, the reaction is carried out in the presence of 0.01 to 10 equivalents of an additive, preferred are 0.2 to 3 equivalents. The equivalents are calculated on the basis of the compound of the formula (III). Suitable additives are acids or bases. Suitable acids are strong inorganic acids, such as hydrochloric acid or sulfuric acid, or strong organic acids, such as acetic acid, methanesulfonic acid or trifluoroacetic acid, or mixtures thereof; preferred is methanesulfonic acid. Suitable bases are organic bases, such as organic nitrogen-bases. Suitable organic nitrogen-bases are trialkylamine bases, such as triethylamine, trimethylamine, Hünigs base, N-methylpyrrolidine, N-methylmorpholine o N-methylpiperidine.

In one embodiment of this preferred embodiment an acid is used as an additive. In another embodiment of this preferred embodiment a base is used as an additive.

The above-described preferred embodiment of the process according to the invention is explained in greater detail by way of the following examples:

EXAMPLE 7

Preparation of 5-amino-9-isopropyl-benzonorbornene (Syn/Anti-Mixture, Syn-Enriched) (Compound No. 1.12)

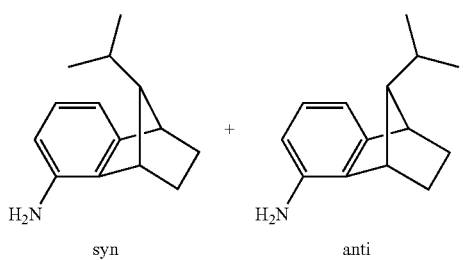

a) Testing of Different Additives at 10 Bar 500 mg (1.7 mmol) of N-Benzyl-5-amino-9-isopropylidene-benzonorbornadiene [Compound No. 3.12, prepared as described in Example 5] dissolved in 5 ml methanol was exhaustively hydrogenated in the presence of 5% Pd/C (50 mg) at ambient temperature and 10 bar during 19 hours. Thus, a mixture of the syn/anti-5-amino-9-isopropyl-benzonorbornenes was obtained. The identity of the reaction product, the epimeric purity (in % syn) and the yield (in %) was assessed via gas chromatography.

| Acid additive | % syn | % yield |
|---|---|---|
| 0.3 equivalents hydrochloric acid | 81 | 85 |
| 0.75 equivalents hydrochloric acid | 78 | 89 |
| 2 equivalents acetic acid | 78 | 86 |
| 5 equivalents acetic acid | 77 | 83 |
| 2 equivalents trifluoroacetic acid | 81 | 91 |
| 5 equivalents trifluoroacetic acid | 82 | 92 |
| 2 equivalents methane sulfonic acid | 88 | 97 |
| 5 equivalents methane sulfonic acid | 88 | 97 | b) Testing of Methane Sulfonic Acid as Additive at Different Pressures 58.8 g (200 mmol) of N-Benzyl-5-amino-9-isopropylidene-benzonorbornadiene [Compound No. 3.12, prepared as described in Example 5] dissolved in methanol was exhaustively hydrogenated in the presence of 5% Pd/C (1 mol %) at ambient temperature during 3-18 hours. Thus, a mixture of the syn/anti-5-amino-9-isopropyl-benzonorbornenes was obtained. The product was isolated and the epimeric purity (in % syn), the yield (in %) and the purity was assessed.

| Pressure | % syn | % yield | % purity |
|---|---|---|---|
| 3 bar | 82 | 94 | 95 |
| 6 bar | 83 | 95 | 97 |
| 12 bar | 81 | 92 | 92 |

In yet another preferred embodiment of the present invention, the reducing agent used in the process for the preparation of the compound of the general formula (IV) from the compound of the general formula (VI) is hydrogen in the presence of a metal catalyst selected from rhodium, palladium and platin.

This preferred embodiment makes it possible to prepare in a simple manner compounds of formula (IV) in which the ratio of the syn epimer of formula (IVa)

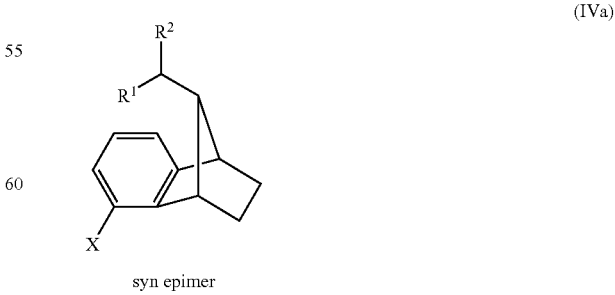

(IVa)

syn epimer to the anti epimer of formula (Ib)

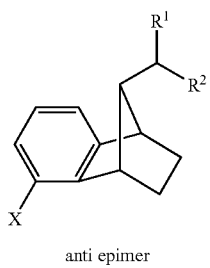

anti epimer (IVb)

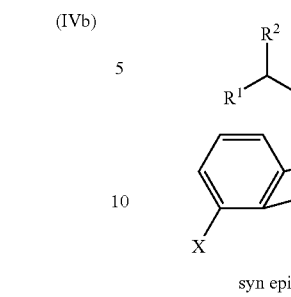

syn epimer (IVa)

is significantly enriched; usually, a syn/anti ratio of more than 55:45 can be achieved; typically a syn/anti ratio of from 60:40 to 99:1 can be achieved. It is therefore a particular advantage of this preferred embodiment that mixtures of compounds of formula IV can be prepared in simple manner that have a syn/anti ratio in favour of the syn epimer.

In this preferred embodiment of the process according to the invention, a compound of the general formula (VI):

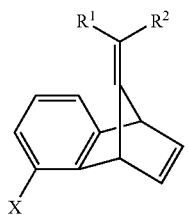

(VI)

wherein $R^1$ and $R^2$ are independently H or $C_{1-6}$ alkyl and X is chloro or bromo, is reacted with hydrogen in the presence of a catalyst selected from rhodium, palladium and platin to form a compound of the general formula (IV)

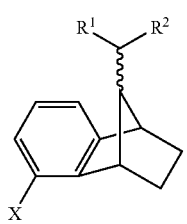

(IV)

wherein $R^1$ and $R^2$ are independently H or $C_{1-6}$ alkyl and X is chloro or bromo, and wherein the ratio of the syn epimer of formula (IVa)

wherein $R^1$, $R^2$ and X are as defined for formula (VI), to the anti epimer of formula (Ib)

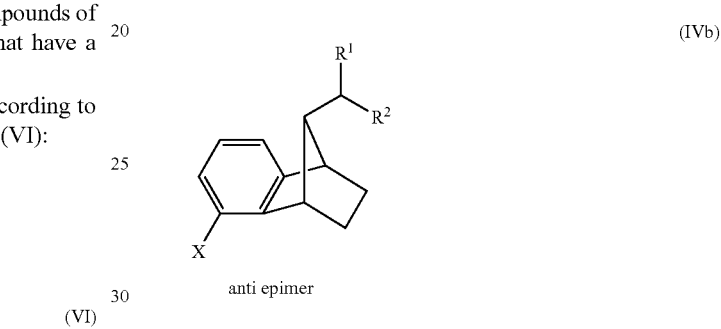

anti epimer (IVb)

wherein $R^1$, $R^2$ and X are as defined for formula (VI), is more than 55:45.

In a particular embodiment, compounds of formula (I) are prepared in which the ratio of the syn epimer of formula (Ia) to the anti epimer of formula (Ib) is from 75:25 to 98:2; preferably from 80:20 to 95:5; more preferably from 90:10 to 95:5.

In a preferred embodiment, X is chloro.

Suitable rhodium catalysts are, for example, rhodium on carbon, rhodium on alumina or rhodium(III) oxide. Preference is given to rhodium on carbon. Suitable palladium catalysts are, for example, heterogenous palladium catalysts, such as palladium on carbon, palladium on aluminium oxide, palladium on silica, palladium on barium carbonate, palladium on barium sulfate, palladium on calcium carbonate or homogenous palladium catalysts, such as palladium acetate, palladium chloride, palladium hydroxide or palladium oxide, or mixtures thereof. Special preference is given to palladium on carbon. Suitable platin catalysts are, for example, platinum on carbon or platinum(IV) oxide. Special preference is given to platinum on carbon.

In one embodiment of this preferred embodiment of the invention, the catalyst is rhodium on carbon.

In another embodiment of this preferred embodiment of the invention, the catalyst is palladium on carbon.

In one embodiment of this preferred embodiment of the invention, the catalyst is platinum on carbon.

Suitable amounts of catalyst are 0.01 to 10 mol % calculated on the basis of the compound of formula (III); preferred are 0.1 to 1 mol %.

The reaction is preferably carried out in the presence of an inert solvent. Suitable solvents are, for example, alcohols, such as methanol, ethanol, propanol or isopropanol, or aprotic solvents, such as tetrahydrofuran, tert-butyl methyl ether, ethyl acetate, dioxane or toluene, and mixtures thereof; special preference is given to ethanol or methanol.

The temperatures are generally varying from 0° C. to 80° C., with preference being given to a range from 0° C. to 45° C., more preferred is a range of 20° C. to 45° C., even more preferred is a range of 20° C. to 30° C.

The reaction time is generally from 1 to 100 hours, preferably from 1 to 24 hours.

Preferably the reaction is carried out at a pressure of at least 2 bar, more preferred is a pressure from 2 to 50 bar, even more preferred 5 to 50 bar. In one embodiment of the invention a pressure from 7 to 20 bar is used, preferably 7 to 15 bar, more preferably 8 to 12 bar.

In a special embodiment of this preferred embodiment of the invention, the reaction is carried out in the presence of 0.01 to 10 equivalents of an additive, preferred are 0.2 to 3 equivalents. The equivalents are calculated on the basis of the compound of the formula (III). Suitable additives are acids or bases. Suitable acids are strong inorganic acids, such as hydrochloric acid or sulfuric acid, or strong organic acids, such as acetic acid, methanesulfonic acid or trifluoroacetic acid, or mixtures thereof; preferred acids are hydrochloric acid, acetic acid, methanesulfonic acid or trifluoroacetic acid. Suitable bases are organic bases, such as organic nitrogen-bases. Suitable organic nitrogen-bases are trialkylamine bases, such as triethylamine, trimethylamine, Hünigs base, N-methylpyrrolidine, N-methylmorpholine o N-methylpiperidine.

In one embodiment of this preferred embodiment an acid is used as an additive. In another embodiment of this preferred embodiment a base is used as an additive.

The above-described preferred embodiment of the process according to the invention is explained in greater detail by way of the following examples:

EXAMPLE 8

Preparation of 5-chloro-9-isopropyl-benzonorbornene (Syn/Anti-Mixture, Syn-Enriched) (Compound. No. 4.26)

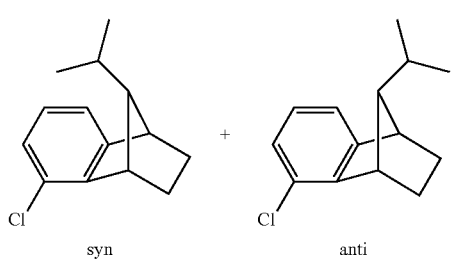

a) Using Pd/C as Catalyst Without Additive 300 mg (1.4 mmol) of 5-Chloro-9-isopropylidene-benzonorbornadiene prepared as described in Example 2) dissolved in 3 ml methanol was exhaustively hydrogenated in the presence of 5% Pd/C (9 mg) at ambient temperature and 10 bar during 16 hours. Thus, a mixture of the syn/anti-5-chloro-9-isopropyl-benzonorbornenes was obtained (epimeric purity: 93% syn; yield: 85%). The identity of the reaction product, the epimeric purity (in % syn) and the yield (in %) was assessed via gas chromatography.

b) Testing of Pd/C as Catalyst Using Different Additives 300 mg (1.4 mmol) of 5-Chloro-9-isopropylidene-benzonorbornadiene prepared as described in Example 2) dissolved in 3 ml methanol was exhaustively hydrogenated in the presence of 5% Pd/C (9 mg) at ambient temperature and 10 bar during 16 hours. Thus, a mixture of the syn/anti-5-chloro-9-isopropyl-benzonorbornenes was obtained The identity of the reaction product, the epimeric purity (in % syn) and the yield (in %) was assessed via gas chromatography.

| Acid additive | % syn | % yield |
|---|---|---|
| 0.5 equivalents hydrochloric acid | 92 | 89 |
| 2 equivalents methane sulfonic acid | 92 | 89 |
| 2 equivalents acetic acid | 94 | 80 | c) Testing of Pt/C as Catalyst Using Different Additives 300 mg (1.4 mmol) of 5-Chloro-9-isopropylidene-benzonorbornadiene prepared as described in Example 2) dissolved in 3 ml methanol was exhaustively hydrogenated in the presence of 5% Pt/C (15 mg) at ambient temperature and 10 bar during 16 hours. Thus, a mixture of the syn/anti-5-chloro-9-isopropyl-benzonorbornenes was obtained The identity of the reaction product, the epimeric purity (in % syn) and the yield (in %) was assessed via gas chromatography.

| Acid additive | % syn | % yield |
|---|---|---|
| 0.5 equivalents hydrochloric acid | 94 | 95 |
| 2 equivalents methane sulfonic acid | 94 | 94 |
| 2 equivalents acetic acid | 94 | 94 |
| 2 equivalents trifluoroacetic acid | 94 | 94 |

The invention claimed is:

1. A process for the preparation of the compound of formula (I):

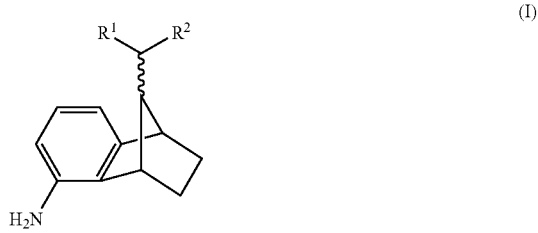

wherein $R^1$ and $R^2$ are independently H or $C_{1-6}$ alkyl, which comprises treating with a reducing agent either a compound of formula (II):

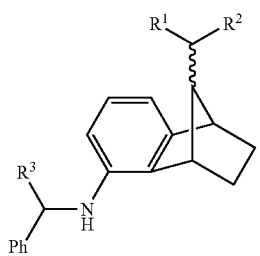

(II)

wherein $R^3$ is H or $C_{1-4}$ alkyl and Ph is phenyl, or a compound of formula (III):

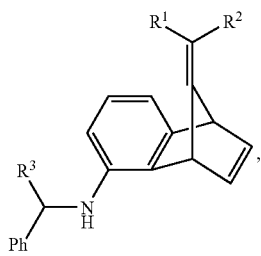

(III)

the reducing agent being effective to cleave the benzyl moiety Ph-CH($R^3$)— from the benzylamino moiety PhCH($R^3$)NH— in the compound of the formula (II) or in the compound of the formula (III) to leave an amino group and, in addition, in the case of the compound of the formula (III), to reduce both the 2,3-double bond and the double bond joining the $R^1R^2C$— moiety to the 9-position of the benzonorbornene ring to single bonds.

2. A process for the preparation of the compound of formula (II)

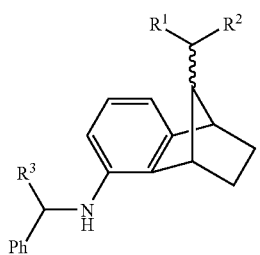

(II)

wherein $R^1$ and $R^2$ are independently H or $C_{1-6}$ alkyl, $R^3$ is H or $C_{1-4}$ alkyl and Ph is phenyl, which comprises (A) reacting a compound of formula (IV):

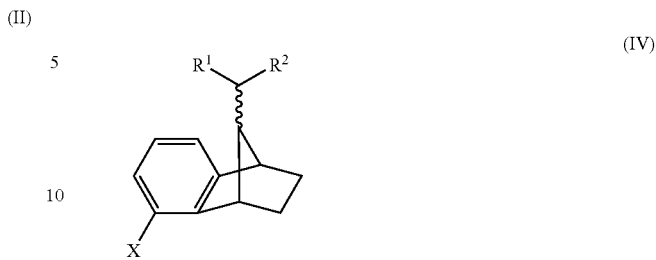

(IV)

wherein X is chloro or bromo, with a benzylamine of formula (V):

(V)

in the presence of a base and a catalytic amount of at least one palladium complex or (B) treating a compound of formula (III):

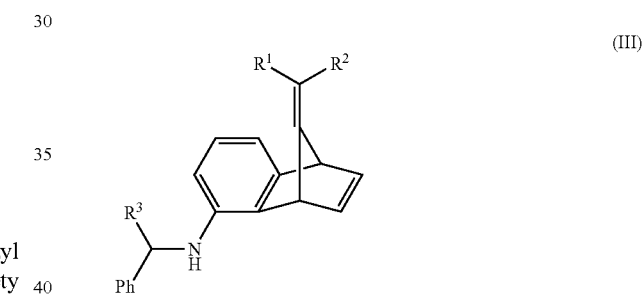

(III)

with a reducing agent, the reducing agent being effective to reduce both the 2,3-double bond and the double bond joining the $R^1R^2C$— moiety to the 9-position of the benzonorbornene ring to single bonds but to leave the PhCH($R^3$)NH— moiety intact.

3. A process for the preparation of the compound of formula (III)

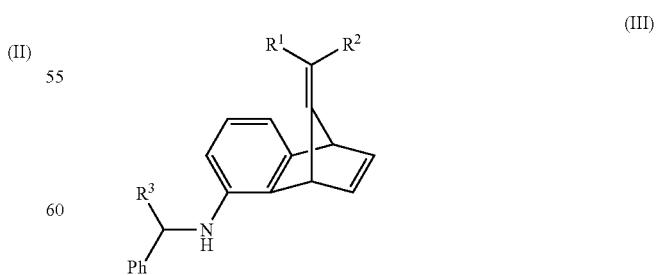

(III)

wherein $R^1$ and $R^2$ are independently H or $C_{1-6}$ alkyl, $R^3$ is H or $C_{1-4}$ alkyl and Ph is phenyl, which comprises reacting a compound of formula (VI):

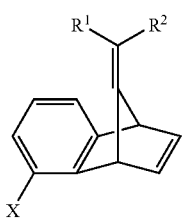

wherein X is chloro or bromo, with a benzylamine of formula (V):

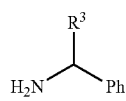

in the presence of a base and a catalytic amount of at least one palladium complex.

4. The process for the preparation of the compound of formula (II) as defined in claim 2 which comprises treating a compound of formula (III):

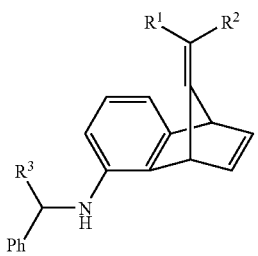

with a reducing agent, the reducing agent being effective to reduce both the 2,3-double bond and the double bond joining the $R^1R^2C-$ moiety to the 9-position of the benzonorbornene ring to single bonds but to leave the PhCH($R^3$)NH— moiety intact.

5. A process for the preparation of the compound of formula (IV)

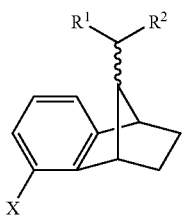

wherein $R^1$ and $R^2$ are independently H or $C_{1-6}$ alkyl and X is chloro or bromo;

which comprises treating a compound of formula (VI):

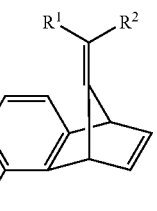

with a reducing agent, the reducing agent being effective to reduce both the 2,3-double bond and the double bond joining the $R^1R^2C-$ moiety to the 9-position of the benzonorbornene ring to single bonds.

6. A process for the preparation of the compound of formula (VI)

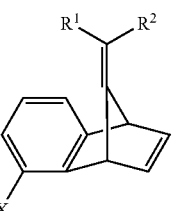

wherein $R^1$ and $R^2$ are independently H or $C_{1-6}$ alkyl and X is chloro or bromo
which comprises reacting a halobenzyne of the formula (VII):

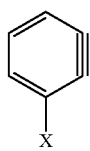

with a fulvene of formula (VIII):

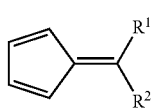

in an inert organic solvent.

7. A process for the preparation of the halobenzyne of formula (VII)

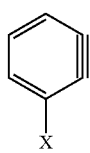

wherein X is chloro or bromo;
which comprises reacting a 1,2,3-trihalobenzene of the formula (IX) or (X):

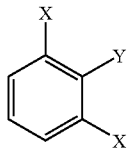
(IX)

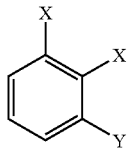
(X)

wherein Y is bromo or iodo, with an organometallic species in an inert atmosphere.

9. The process for the preparation of a compound of formula (I) according to claim 1 which comprises the steps of
   (a) reacting a compound of formula (IV):

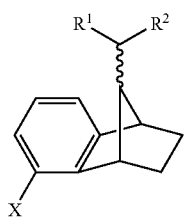
(IV)

wherein X is chloro or bromo, with a benzylamine of formula (V):

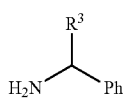
(V)

in the presence of a base and a catalytic amount of at least one palladium complex to form a compound of formula (II):

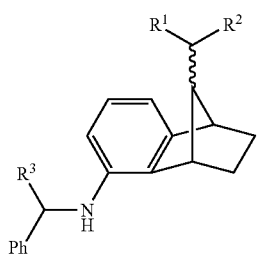
(II)

and
(b) treating the compound of formula (II) so formed with a reducing agent, the reducing agent being effective to cleave the benzyl moiety Ph-CH(R³)— from the benzylamino moiety PhCH(R³)NH— to leave an amino group.

9. The process for the preparation of a compound of formula (I) according to claim 1 which comprises the steps of
   (a) reacting a compound of formula (VI):

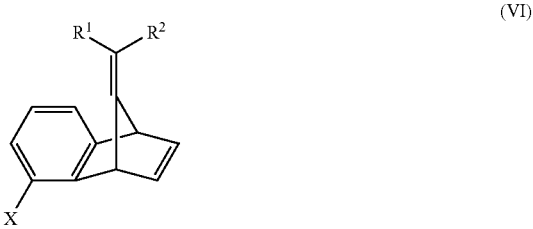
(VI)

wherein X is chloro or bromo, with a benzylamine of formula (V):

(V)

in the presence of a base and a catalytic amount of at least one palladium complex to form a compound of formula (III):

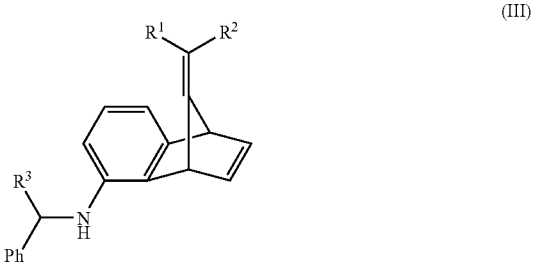
(III)

and
(b) treating the compound of formula (III) so formed with a reducing agent, the reducing agent being effective to cleave the benzyl moiety Ph-CH(R³)— from the benzylamino moiety PhCH(R³)NH— to leave an amino group and to reduce both the 2,3-double bond and the double bond joining the R¹R²C— moiety to the 9-position of the benzonorbornene ring to single bonds.

10. The process for the preparation of a compound of formula (I) according to claim 1 which comprises the steps of (a) treating a compound of formula (VI):

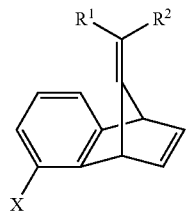
(VI)

wherein X is chloro or bromo, with a reducing agent, the reducing agent being effective to reduce both the 2,3-double bond and the double bond joining the $R^1R^2C$— moiety to the 9-position of the benzonorbornene ring to single bonds to form a compound of formula (IV):

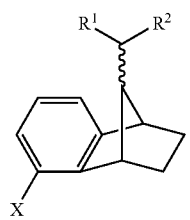
(IV)

(b) reacting the compound of formula (IV) so formed with a benzylamine of formula (V):

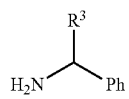
(V)

in the presence of a base and a catalytic amount of at least one palladium complex to form a compound of formula (II):

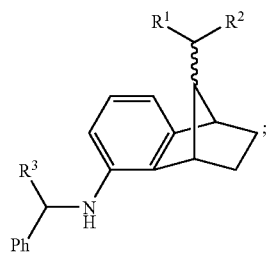
(II)

and (c) treating the compound of formula (II) so formed with a reducing agent, the reducing agent being effective to cleave the benzyl moiety Ph-CH($R^3$)— from the benzylamino moiety PhCH($R^3$)NH— to leave an amino group.

11. The process for the preparation of a compound of formula (I) according to claim 1 which comprises the steps of (a) reacting a compound of formula (VI):

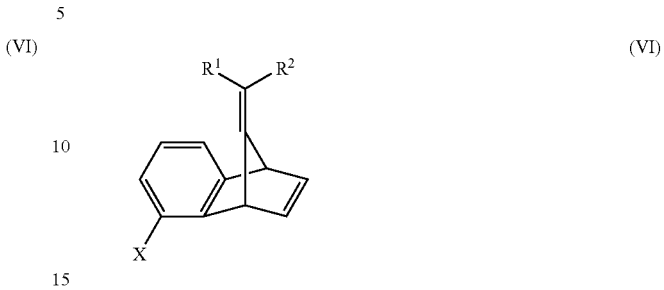
(VI)

wherein X is chloro or bromo, with a benzylamine of formula (V):

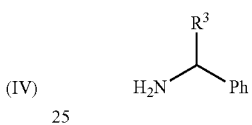
(V)

in the presence of a base and a catalytic amount of at least one palladium complex to form a compound of formula (III):

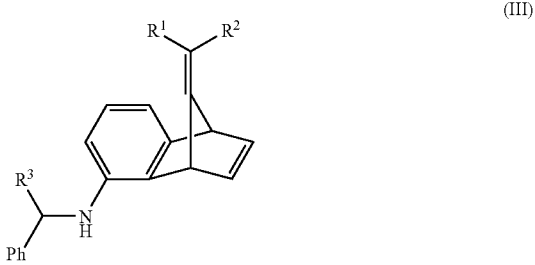
(III)

(b) treating the compound of formula (III) so formed with a reducing agent, the reducing agent being effective to reduce both the 2,3-double bond and the double bond joining the $R^1R^2C$— moiety to the 9-position of the benzonorbornene ring to single bonds but to leave the PhCH($R^3$)NH— moiety intact to form a compound of formula (II):

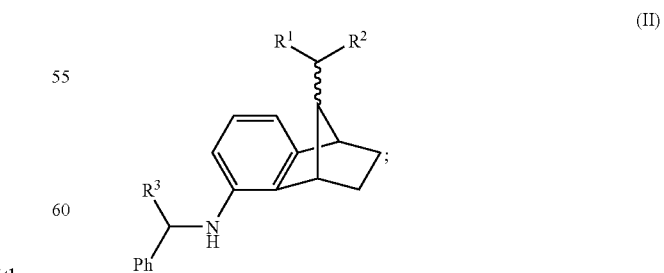
(II)

and (c) treating the compound of formula (II) so formed with a reducing agent, the reducing agent being effective to cleave the benzyl moiety Ph-CH(R³)— from the benzylamino moiety PhCH(R³)NH— to leave an amino group.

12. A process for the preparation of a compound of formula (VI)

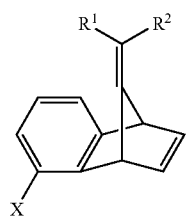

(VI)

wherein R¹ and R² are independently H or $C_{1-6}$ alkyl and X is chloro or bromo;

which comprises reacting a 1,2,3-trihalobenzene of the formula (IX) or (X):

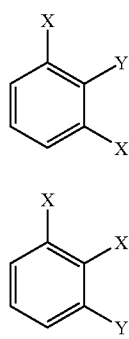

(IX)

(X)

wherein Y is bromo or iodo, with an organometallic species in the presence of a fulvene of formula (VIII):

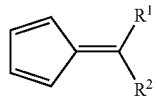

(VIII)

in an inert organic solvent and in an inert atmosphere.

13. The process for the preparation of a compound of formula (I) according to claim 1 which comprises the steps of (a) reacting a 1,2,3-trihalobenzene of the formula (IX) or (X):

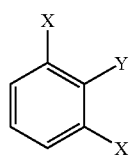

(IX)

(X)

wherein X is chloro or bromo and Y is bromo or iodo, with an organometallic species in an inert atmosphere to form a halobenzyne of formula (VII):

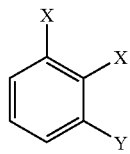

(VII)

(b) reacting the halobenzyne of formula (VII) so formed with a fulvene of formula (VIII):

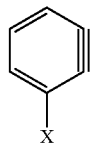

(VIII)

in an inert organic solvent to form a compound of formula (VI):

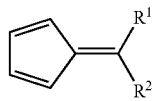

(VI)

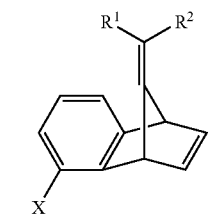

(c) reacting the compound of the general formula (VI) so formed with a benzylamine of formula (V):

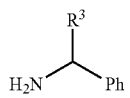

(V)

in the presence of a base and a catalytic amount of at least one palladium complex to form a compound of formula (III):

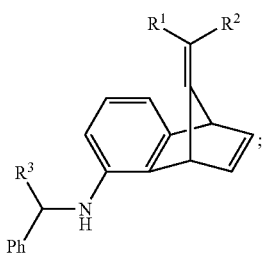
(III)

and (d) treating the compound of formula (III) so formed with a reducing agent, the reducing agent being effective to cleave the benzyl moiety Ph-CH($R^3$)— from the benzylamino moiety PhCH($R^3$)NH— to leave an amino group and to reduce both the 2,3-double bond and the double bond joining the $R^1R^2C$— moiety to the 9-position of the benzonorbornene ring to single bonds.

14. The process for the preparation of a compound of formula (I) according to claim 1 which comprises the steps of (a) reacting a 1,2,3-trihalobenzene of the formula (IX) or (X):

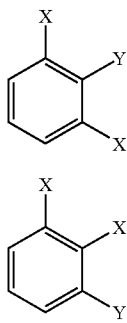
(IX)

(X)

wherein X is chloro or bromo and Y is bromo or iodo, with an organometallic species in an inert atmosphere to form a halobenzyne of formula (VII):

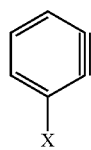
(VII)

(b) reacting the halobenzyne of formula (VII) so formed with a fulvene of formula (VIII):

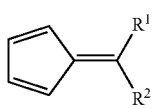
(VIII)

in an inert organic solvent to form a compound of formula (VI):

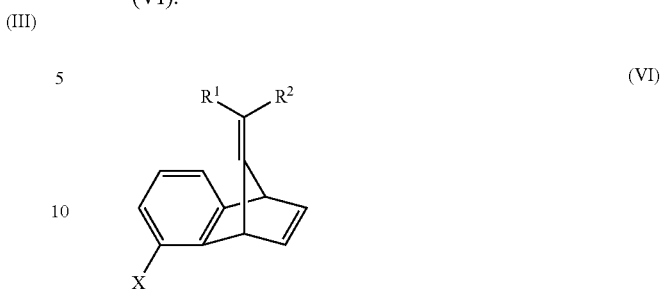
(VI)

(c) treating a compound of formula (VI) so formed with a reducing agent, the reducing agent being effective to reduce both the 2,3-double bond and the double bond joining the $R^1R^2C$— moiety to the 9-position of the benzonorbornene ring to single bonds to form a compound of formula (IV):

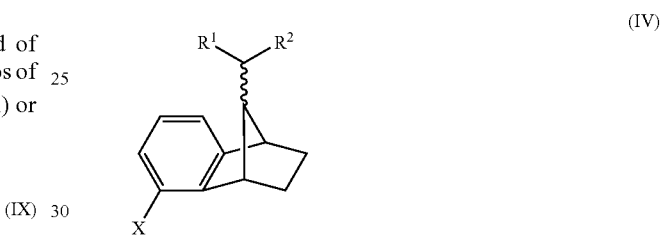
(IV)

(d) reacting the compound of formula (IV) so formed with a benzylamine of formula (V):

(V)

in the presence of a base and a catalytic amount of at least one palladium complex to form a compound of formula (II):

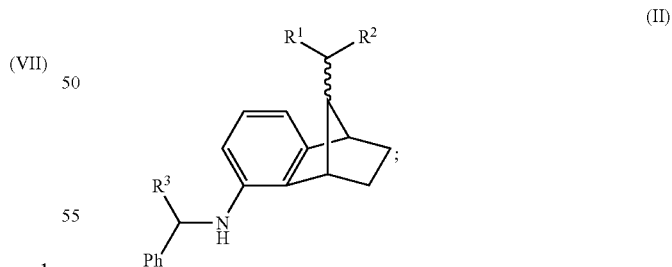
(II)

and (e) treating the compound of formula (II) so formed with a reducing agent, the reducing agent being effective to cleave the benzyl moiety Ph-CH($R^3$)— from the benzylamino moiety PhCH($R^3$)NH— to leave an amino group.

15. The process for the preparation of a compound of the general formula (I) according to claim 1 which comprises the steps of (a) reacting a 1,2,3-trihalobenzene of the formula (IX) or (X):

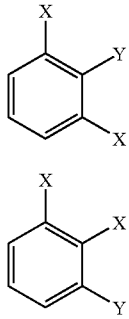

wherein X is chloro or bromo and Y is bromo or iodo, with an organometallic species in an inert atmosphere to form a halobenzyne of formula (VII):

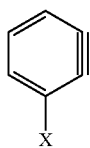

(b) reacting the halobenzyne of the general formula (VII) so formed with a fulvene of formula (VIII):

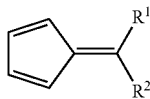

in an inert organic solvent to form a compound of formula (VI):

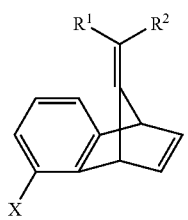

(c) reacting the compound of formula (VI) so formed with a benzylamine of formula (V):

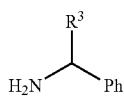

in the presence of a base and a catalytic amount of at least one palladium complex to form a compound of formula (III):

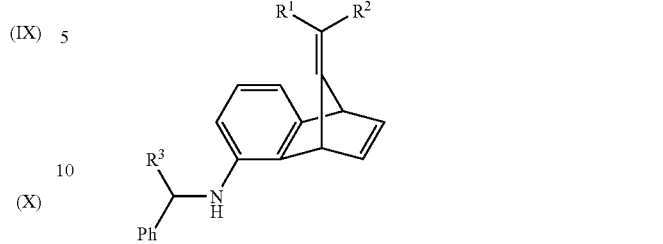

(d) treating the compound of formula (III) so formed with a reducing agent, the reducing agent being effective to reduce both the 2,3-double bond and the double bond joining the $R^1R^2C-$ moiety to the 9-position of the benzonorbornene ring to single bonds but to leave the $PhCH(R^3)NH-$ moiety intact to form a compound of the general formula (II):

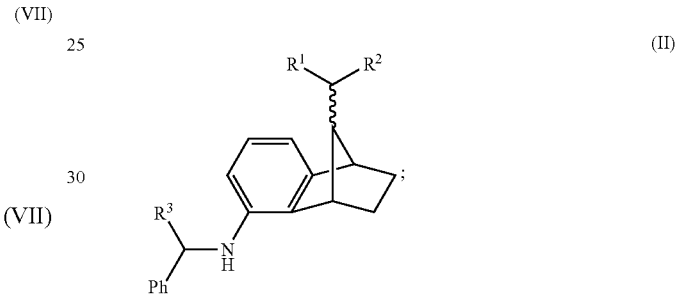

and (e) treating the compound of formula (II) so formed with a reducing agent, the reducing agent being effective to cleave the benzyl moiety $Ph\text{-}CH(R^3)-$ from the benzylamino moiety $PhCH(R^3)NH-$ to leave an amino group.

16. A compound of formula (II), (III), (IV) or (VI):

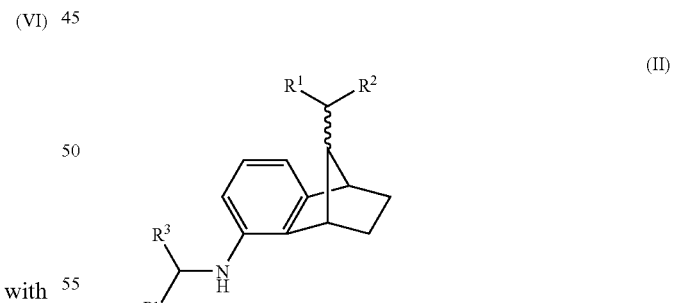

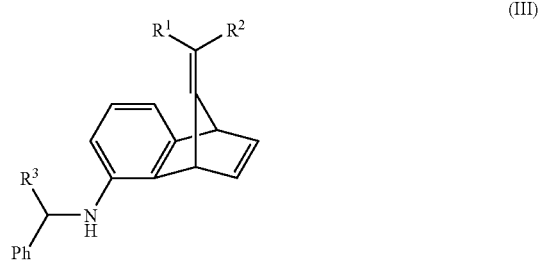

-continued

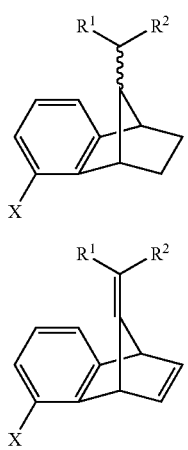
(IV)

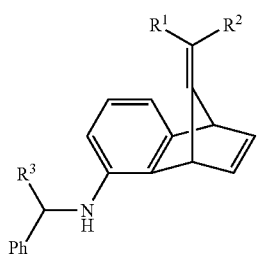
(VI)

wherein $R^1$ and $R^2$ are independently H or $C_{1-6}$ alkyl, $R^3$ is H or $C_{1-4}$ alkyl, Ph is phenyl and X is chloro or bromo.

17. The process according to claim 1, wherein a compound of the formula (III)

(III)

is reacted with hydrogen in the presence of a palladium catalyst to form a compound of formula (I)

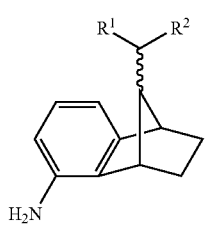
(I)

and wherein the ratio of the syn epimer of formula (Ia)

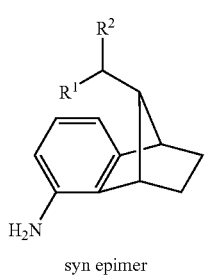
(Ia)

syn epimer to the anti epimer of formula (Ib)

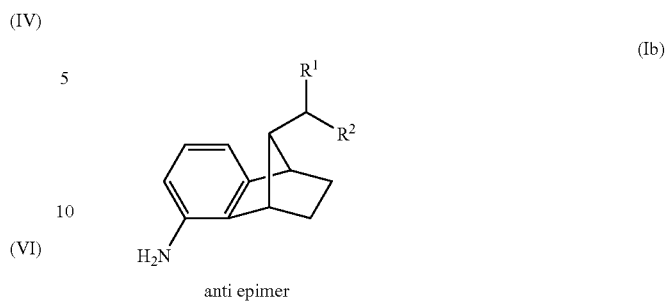
(Ib)

anti epimer is more than 55:45.

18. The process according to claim 17, wherein the process is carried out in the presence of an additive, wherein the additive is an acid or a base.

19. The process according to claim 17, wherein the process is carried out at a temperature from 0° C. to 80° C.

20. The process according to claim 17, wherein the process is carried out at a pressure of at least 2 bar.

21. The process according to claim 5, wherein a compound of the formula (VI)

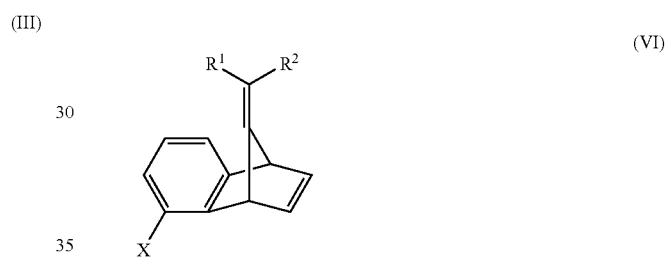
(VI)

is reacted with hydrogen in the presence of a catalyst selected from rhodium, palladium and platinum, to form a compound of formula (IV)

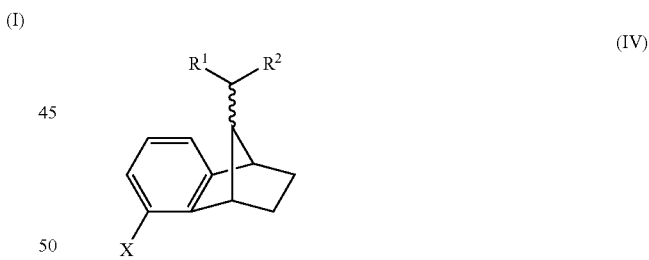
(IV)

and wherein the ratio of the syn epimer of formula (IVa)

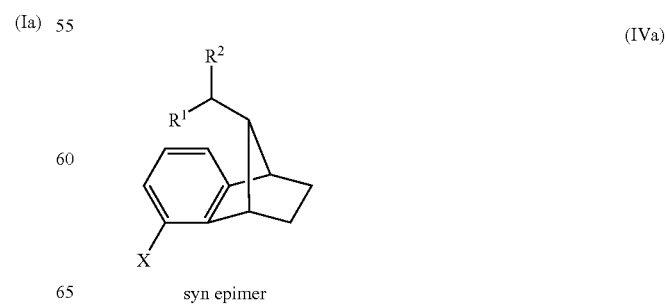
(IVa)

syn epimer to the anti epimer of formula (IVb)

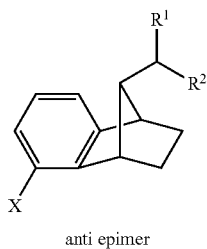
(IVb)

anti epimer is more than 55:45.

22. The process according to claim 21, wherein X is chloro.

23. The process according to claim 21, wherein the catalyst is a palladium catalyst.

24. The process according to claim 21, wherein the catalyst is a platinum catalyst.

25. The process according to claim 21, wherein the process is carried out in the presence of an additive, wherein the additive is an acid or a base.

26. The process according to claim 21, wherein the process is carried out at a temperature from 0° C. to 80° C.

27. The process according to claim 21, wherein the process is carried out at a pressure of at least 2 bar.

* * * * *